(12) United States Patent
Lin et al.

(10) Patent No.: US 10,539,478 B2
(45) Date of Patent: *Jan. 21, 2020

(54) DETECTION OF MISALIGNMENT OF ROBOTIC ARMS

(71) Applicant: Auris Health, Inc., Redwood City, CA (US)

(72) Inventors: Jiayi Lin, San Mateo, CA (US); Shu-Yun Chung, San Jose, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/026,591

(22) Filed: Jul. 3, 2018

(65) Prior Publication Data

US 2019/0107454 A1    Apr. 11, 2019

Related U.S. Application Data

(63) Continuation of application No. 15/729,569, filed on Oct. 10, 2017, now Pat. No. 10,145,747.

(51) Int. Cl.
*G01L 5/00* (2006.01)
*G01L 5/22* (2006.01)
(Continued)

(52) U.S. Cl.
CPC .............. *G01L 5/226* (2013.01); *A61B 34/20* (2016.02); *A61B 34/32* (2016.02); *A61B 90/06* (2016.02);
(Continued)

(58) Field of Classification Search
CPC ......... G01L 5/226; A61B 34/20; A61B 34/30; A61B 34/32; A61B 90/06; A61B 90/08;
(Continued)

(56) References Cited

U.S. PATENT DOCUMENTS 4,644,237 A    2/1987  Frushour et al.
4,745,908 A    5/1988  Wardle
(Continued)

FOREIGN PATENT DOCUMENTS

DE    102013100605    7/2014
EP    1 250 986    10/2002
(Continued)

OTHER PUBLICATIONS

Kukuk, Oct. 5, 2001, TBNA-protocols: Guiding TransBronchial Needle Aspirations Without a Computer in the Operating Room, MICCAI 2001, 2208:997-1006.
(Continued)

*Primary Examiner* — Max H Noori
(74) *Attorney, Agent, or Firm* — Knobbe, Martens, Olson & Bear, LLP

(57) ABSTRACT

Certain aspects relate to systems and techniques for detection of undesirable forces on one or more surgical robotic arms. In one aspect, there is provided a system including a robotic arm, including: two linkages, a joint, a torque sensor, and an instrument device manipulator (IDM). The system may further include a processor configured to measure a first torque value at the joint based on an output of the torque sensor and determine a second torque value at the joint based on a position of the robotic arm. The second torque value may be indicative of a gravitational component of the torque between the two linkages. The processor may be further configured to determine a force at the IDM based a difference between the first and second torque values and determine whether the robotic arm has collided with an object or misaligned based on the force at the IDM.

30 Claims, 23 Drawing Sheets

US 10,539,478 B2
Page 2

(51) Int. Cl.
| | |
|---|---|
| *A61B 34/20* | (2016.01) |
| *A61B 90/00* | (2016.01) |
| *A61B 34/32* | (2016.01) |
| A61B 6/03 | (2006.01) |
| A61B 34/30 | (2016.01) |
| A61B 1/267 | (2006.01) |
| A61B 1/273 | (2006.01) |
| A61B 50/13 | (2016.01) |
| A61B 1/307 | (2006.01) |
| A61B 1/313 | (2006.01) |

(52) U.S. Cl.
CPC ............ *A61B 90/08* (2016.02); *A61B 1/2676* (2013.01); *A61B 1/2736* (2013.01); *A61B 1/307* (2013.01); *A61B 1/3132* (2013.01); *A61B 6/032* (2013.01); *A61B 50/13* (2016.02); *A61B 2034/2051* (2016.02); *A61B 2034/301* (2016.02); *A61B 2090/064* (2016.02); *A61B 2090/066* (2016.02); *A61B 2090/0811* (2016.02)

(58) Field of Classification Search
CPC . A61B 1/00006; A61B 1/00149; A61B 9/163; A61B 2034/2051; A61B 2034/301; A61B 46/10; A61B 50/13; A61B 2090/064; A61B 2090/066; A61B 2090/0811; A61B 1/2676; A61B 1/2736; A61B 1/307; A61B 1/3132; A61B 6/032; A61B 2017/00477
USPC .................................................... 73/862.041
See application file for complete search history.

(56) References Cited

U.S. PATENT DOCUMENTS

| | | | |
|---|---|---|---|
| 4,748,969 A | | 6/1988 | Wardle |
| 5,194,791 A | * | 3/1993 | Cull ..................... B25J 17/0208 318/568.1 |
| 5,280,781 A | | 1/1994 | Oku |
| 5,408,263 A | | 4/1995 | Kikuchi |
| 5,672,877 A | | 9/1997 | Liebig et al. |
| 5,899,851 A | | 5/1999 | Koninckx |
| 6,004,016 A | | 12/1999 | Spector |
| 6,198,974 B1 | | 3/2001 | Webster, Jr. |
| 6,246,200 B1 | | 6/2001 | Blumenkranz et al. |
| 6,459,926 B1 | | 10/2002 | Nowlin |
| 6,690,963 B2 | | 2/2004 | Ben-Haim |
| 6,837,846 B2 | | 1/2005 | Jaffe |
| 7,197,354 B2 | | 3/2007 | Sobe |
| 7,607,440 B2 | | 10/2009 | Coste-Maniere et al. |
| 7,772,541 B2 | | 8/2010 | Froggatt et al. |
| 7,963,288 B2 | | 6/2011 | Rosenberg et al. |
| 8,335,557 B2 | | 12/2012 | Maschke |
| 8,376,934 B2 | | 2/2013 | Takahashi |
| 8,396,595 B2 | | 3/2013 | Dariush |
| 8,442,618 B2 | | 5/2013 | Strommer et al. |
| 8,498,691 B2 | | 7/2013 | Moll et al. |
| 8,506,555 B2 | | 8/2013 | Ruiz Morales |
| 8,554,368 B2 | | 10/2013 | Fielding et al. |
| 8,720,448 B2 | | 5/2014 | Reis et al. |
| 8,738,181 B2 | | 5/2014 | Greer et al. |
| 8,827,948 B2 | | 9/2014 | Romo et al. |
| 8,929,631 B2 | | 1/2015 | Pfister et al. |
| 8,945,095 B2 | | 2/2015 | Blumenkranz |
| 9,014,851 B2 | | 4/2015 | Wong et al. |
| 9,129,417 B2 | | 9/2015 | Zheng et al. |
| 9,173,713 B2 | | 11/2015 | Hart et al. |
| 9,199,372 B2 | | 12/2015 | Henderson et al. |
| 9,226,796 B2 | | 1/2016 | Bowling |
| 9,256,940 B2 | | 2/2016 | Carelsen et al. |
| 9,289,578 B2 | | 3/2016 | Walker et al. |
| 9,314,306 B2 | | 4/2016 | Yu |
| 9,345,456 B2 | | 5/2016 | Tsonton et al. |
| 9,358,682 B2 | | 6/2016 | Ruiz Morales |
| 9,504,604 B2 | | 11/2016 | Alvarez |
| 9,522,034 B2 | | 12/2016 | Johnson |
| 9,561,083 B2 | | 2/2017 | Yu et al. |
| 9,622,827 B2 | | 4/2017 | Yu et al. |
| 9,629,595 B2 | | 4/2017 | Walker et al. |
| 9,636,184 B2 | | 5/2017 | Lee et al. |
| 9,675,422 B2 | | 6/2017 | Hourtash et al. |
| 9,713,509 B2 | | 7/2017 | Schuh et al. |
| 9,726,476 B2 | | 8/2017 | Ramamurthy et al. |
| 9,727,963 B2 | | 8/2017 | Mintz et al. |
| 9,737,371 B2 | | 8/2017 | Romo et al. |
| 9,737,373 B2 | | 8/2017 | Schuh |
| 9,744,335 B2 | | 8/2017 | Jiang |
| 9,763,741 B2 | | 9/2017 | Alvarez et al. |
| 9,788,910 B2 | | 10/2017 | Schuh |
| 9,789,608 B2 | | 10/2017 | Itkowitz et al. |
| 9,818,681 B2 | | 11/2017 | Machida |
| 9,844,353 B2 | | 12/2017 | Walker et al. |
| 9,844,412 B2 | | 12/2017 | Bogusky et al. |
| 9,867,635 B2 | | 1/2018 | Alvarez et al. |
| 9,918,681 B2 | | 3/2018 | Wallace et al. |
| 9,931,025 B1 | | 4/2018 | Graetzel et al. |
| 9,949,749 B2 | | 4/2018 | Noonan et al. |
| 9,955,986 B2 | | 5/2018 | Shah |
| 9,962,228 B2 | | 5/2018 | Schuh et al. |
| 9,980,785 B2 | | 5/2018 | Schuh |
| 9,993,313 B2 | | 6/2018 | Schuh et al. |
| 10,016,900 B1 | | 7/2018 | Meyer et al. |
| 10,022,192 B1 | | 7/2018 | Ummalaneni |
| 10,046,140 B2 | | 8/2018 | Kokish et al. |
| 10,080,576 B2 | | 9/2018 | Romo et al. |
| 10,145,747 B1 | | 12/2018 | Lin et al. |
| 10,159,532 B1 | | 12/2018 | Ummalaneni et al. |
| 10,299,870 B2 | | 5/2019 | Connolly et al. |
| 2001/0000040 A1 | | 3/2001 | Adams et al. |
| 2002/0077533 A1 | | 6/2002 | Bieger et al. |
| 2002/0161280 A1 | | 10/2002 | Chatenever et al. |
| 2003/0045778 A1 | | 3/2003 | Ohline |
| 2003/0182091 A1 | | 9/2003 | Kukuk |
| 2004/0257021 A1 | | 12/2004 | Chang et al. |
| 2005/0043718 A1 | | 2/2005 | Madhani |
| 2005/0065400 A1 | | 3/2005 | Banik |
| 2005/0107917 A1 | * | 5/2005 | Smith .................. B25J 15/0253 700/245 |
| 2005/0222554 A1 | | 10/2005 | Wallace et al. |
| 2005/0256398 A1 | | 11/2005 | Hastings |
| 2005/0261551 A1 | | 11/2005 | Couvillon |
| 2005/0272975 A1 | | 12/2005 | McWeeney et al. |
| 2006/0015096 A1 | | 1/2006 | Hauck et al. |
| 2006/0041293 A1 | | 2/2006 | Mehdizadeh |
| 2006/0079745 A1 | | 4/2006 | Viswanathan |
| 2007/0013336 A1 | | 1/2007 | Nowlin et al. |
| 2007/0043455 A1 | | 2/2007 | Viswanathan |
| 2007/0135686 A1 | | 6/2007 | Maschke |
| 2007/0142971 A1 | * | 6/2007 | Schena ................ B25J 19/0029 700/251 |
| 2007/0150155 A1 | | 6/2007 | Kawai |
| 2007/0249911 A1 | | 10/2007 | Simon |
| 2007/0253599 A1 | | 11/2007 | White et al. |
| 2007/0287992 A1 | | 12/2007 | Diolaiti |
| 2007/0299353 A1 | | 12/2007 | Harlev et al. |
| 2008/0027313 A1 | | 1/2008 | Shachar |
| 2008/0046122 A1 | | 2/2008 | Manzo et al. |
| 2008/0108870 A1 | | 5/2008 | Wiita et al. |
| 2008/0123921 A1 | | 5/2008 | Gielen et al. |
| 2008/0140087 A1 | | 6/2008 | Barbagli et al. |
| 2008/0159653 A1 | | 7/2008 | Dunki-Jacobs et al. |
| 2008/0231221 A1 | | 9/2008 | Ogawa |
| 2008/0249640 A1 | | 10/2008 | Vittor et al. |
| 2008/0255505 A1 | | 10/2008 | Carlson et al. |
| 2008/0312771 A1 | | 12/2008 | Sugiura |
| 2009/0076534 A1 | | 3/2009 | Shelton |
| 2009/0184825 A1 | | 7/2009 | Anderson |
| 2009/0198298 A1 | | 8/2009 | Kaiser et al. |
| 2009/0245600 A1 | | 10/2009 | Hoffman |
| 2009/0287354 A1 | | 11/2009 | Choi |
| 2009/0324161 A1 | | 12/2009 | Prisco |
| 2010/0030115 A1 | | 2/2010 | Fujimoto |

(56) References Cited

U.S. PATENT DOCUMENTS

| | | |
|---|---|---|
| 2010/0069920 A1* | 3/2010 | Naylor .............. A61N 5/1049 606/130 |
| 2010/0076263 A1 | 3/2010 | Tanaka |
| 2010/0121138 A1 | 5/2010 | Goldenberg et al. |
| 2010/0234856 A1 | 9/2010 | Stoianovici et al. |
| 2010/0256812 A1 | 10/2010 | Tsusaka et al. |
| 2011/0021926 A1 | 1/2011 | Spencer |
| 2011/0082366 A1 | 4/2011 | Scully et al. |
| 2011/0082462 A1 | 4/2011 | Suarez |
| 2011/0137122 A1 | 6/2011 | Kawai |
| 2011/0153252 A1 | 6/2011 | Govari |
| 2011/0160570 A1 | 6/2011 | Kariv |
| 2011/0196199 A1 | 8/2011 | Donhowe et al. |
| 2011/0257480 A1 | 10/2011 | Takahashi |
| 2011/0258842 A1 | 10/2011 | Dukesherer et al. |
| 2011/0319910 A1 | 12/2011 | Roelle et al. |
| 2012/0000427 A1 | 1/2012 | Nilsson |
| 2012/0046522 A1 | 2/2012 | Naito |
| 2012/0059249 A1 | 3/2012 | Verard et al. |
| 2012/0071752 A1 | 3/2012 | Sewell |
| 2012/0071822 A1 | 3/2012 | Romo et al. |
| 2012/0123441 A1 | 5/2012 | Au |
| 2012/0130217 A1 | 5/2012 | Kauphusman et al. |
| 2012/0209293 A1 | 8/2012 | Carlson |
| 2012/0215094 A1 | 8/2012 | Rahimian et al. |
| 2012/0253276 A1 | 10/2012 | Govari et al. |
| 2012/0283745 A1* | 11/2012 | Goldberg .............. A61B 34/30 606/130 |
| 2012/0328077 A1 | 12/2012 | Bouvier |
| 2013/0018306 A1 | 1/2013 | Ludwin |
| 2013/0085330 A1 | 4/2013 | Ramamurthy et al. |
| 2013/0090530 A1 | 4/2013 | Ramamurthy |
| 2013/0102846 A1 | 4/2013 | Sjostrom |
| 2013/0131503 A1 | 5/2013 | Schneider et al. |
| 2013/0165854 A1 | 6/2013 | Sandhu et al. |
| 2013/0165945 A9 | 6/2013 | Roelle |
| 2013/0218005 A1 | 8/2013 | Desai |
| 2013/0325030 A1 | 12/2013 | Hourtash et al. |
| 2014/0114180 A1 | 4/2014 | Jain |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0222207 A1 | 8/2014 | Bowling et al. |
| 2014/0277333 A1 | 9/2014 | Lewis et al. |
| 2014/0296870 A1 | 10/2014 | Stern et al. |
| 2014/0309649 A1 | 10/2014 | Alvarez et al. |
| 2014/0316420 A1 | 10/2014 | Ballard et al. |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0088161 A1 | 3/2015 | Hata |
| 2015/0101442 A1 | 4/2015 | Romo |
| 2015/0104284 A1 | 4/2015 | Riedel |
| 2015/0119628 A1 | 4/2015 | Bharat et al. |
| 2015/0119638 A1 | 4/2015 | Yu et al. |
| 2015/0164594 A1 | 6/2015 | Romo et al. |
| 2015/0164596 A1 | 6/2015 | Romo |
| 2015/0202015 A1 | 7/2015 | Elhawary |
| 2015/0223902 A1 | 8/2015 | Walker et al. |
| 2015/0265359 A1 | 9/2015 | Camarillo |
| 2015/0265807 A1 | 9/2015 | Park et al. |
| 2015/0335480 A1 | 11/2015 | Alvarez et al. |
| 2015/0342695 A1 | 12/2015 | He |
| 2015/0359597 A1 | 12/2015 | Gombert et al. |
| 2015/0374956 A1 | 12/2015 | Bogusky |
| 2016/0001038 A1 | 1/2016 | Romo et al. |
| 2016/0005168 A1 | 1/2016 | Merlet |
| 2016/0005220 A1 | 1/2016 | Weingarten |
| 2016/0005576 A1 | 1/2016 | Tsukamoto |
| 2016/0016319 A1 | 1/2016 | Remirez |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper |
| 2016/0075030 A1* | 3/2016 | Takahashi .............. B25J 9/1694 700/253 |
| 2016/0081568 A1 | 3/2016 | Kolberg |
| 2016/0100772 A1 | 4/2016 | Ikuma |
| 2016/0228032 A1 | 8/2016 | Walker et al. |
| 2016/0270865 A1 | 9/2016 | Landey et al. |
| 2016/0278865 A1 | 9/2016 | Capote |
| 2016/0287053 A1 | 10/2016 | Miura |
| 2016/0287111 A1 | 10/2016 | Jacobsen |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0331469 A1 | 11/2016 | Hall et al. |
| 2016/0338787 A1 | 11/2016 | Popovic |
| 2016/0346038 A1 | 12/2016 | Helgeson |
| 2016/0346924 A1 | 12/2016 | Hasegawa |
| 2016/0354057 A1 | 12/2016 | Hansen et al. |
| 2016/0360947 A1 | 12/2016 | Iida |
| 2016/0360949 A1 | 12/2016 | Hyodo |
| 2016/0374541 A1 | 12/2016 | Agrawal et al. |
| 2017/0007337 A1 | 1/2017 | Dan |
| 2017/0056215 A1 | 3/2017 | Nagesh et al. |
| 2017/0068796 A1 | 3/2017 | Passerini et al. |
| 2017/0100199 A1 | 4/2017 | Yu et al. |
| 2017/0119413 A1 | 5/2017 | Romo |
| 2017/0119481 A1 | 5/2017 | Romo et al. |
| 2017/0151027 A1 | 6/2017 | Walker et al. |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0251988 A1 | 9/2017 | Weber et al. |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0304015 A1 | 10/2017 | Tavallaei et al. |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0250085 A1 | 9/2018 | Simi |
| 2018/0271604 A1* | 9/2018 | Grout .............. A61B 34/30 |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0167367 A1 | 6/2019 | Walker et al. |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0209252 A1 | 7/2019 | Walker et al. |

(56) References Cited

U.S. PATENT DOCUMENTS

| | | |
|---|---|---|
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |

FOREIGN PATENT DOCUMENTS

| | | |
|---|---|---|
| EP | 1 566 150 | 8/2005 |
| EP | 3 025 630 | 6/2006 |
| EP | 1 800 593 | 6/2007 |
| EP | 2 158 834 | 3/2010 |
| EP | 2 392 435 | 12/2011 |
| WO | WO 01/56457 | 8/2001 |
| WO | WO 04/029782 | 4/2004 |
| WO | WO 05/087128 | 9/2005 |
| WO | WO 06/122061 | 11/2006 |
| WO | WO 09/120940 | 10/2009 |
| WO | WO 11/132409 | 10/2011 |
| WO | WO 15/142957 | 9/2015 |
| WO | WO 17/048194 | 3/2017 |

OTHER PUBLICATIONS

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

Blankenstein, Jun. 2008, Dynamic Registration and High Speed Visual Servoing in Robot-Assisted Surgery, Katholieke Universiteit Leuven, Leuven, Belgium.

\* cited by examiner

DETECTION OF MISALIGNMENT OF ROBOTIC ARMS

CROSS-REFERENCE TO RELATED APPLICATION

This application is a continuation of application Ser. No. 15/729,569, filed Oct. 10, 2017, which is hereby incorporated by reference in its entirety.

TECHNICAL FIELD

The systems and methods disclosed herein are directed to surgical robotic systems, and more particularly to detecting undesirable forces on one or more robotic arms in a surgical robotic system.

BACKGROUND

Medical procedures such as endoscopy (e.g., bronchoscopy) may involve the insertion of a medical tool into a patient's luminal network (e.g., airways) for diagnostic and/or therapeutic purposes. Surgical robotic systems may be used to control the insertion and/or manipulation of the steerable instrument tool during a medical procedure. The surgical robotic system may comprise at least one robotic arm including an instrument device manipulator (IDM) assembly which may be used to control the positioning of the steerable instrument during the medical procedure.

SUMMARY

The systems, methods and devices of this disclosure each have several innovative aspects, no single one of which is solely responsible for the desirable attributes disclosed herein.

In one aspect, there is provided a system comprising: a first robotic arm, comprising: at least two linkages, at least one joint connecting the at least two linkages, at least one torque sensor configured to detect torque between the at least two linkages, and an instrument device manipulator (IDM) connected to a distal end of the first robotic arm; a processor; and a memory storing computer-executable instructions to cause the processor to: measure a first torque value at the at least one joint based on an output of the torque sensor, determine a second torque value at the at least one joint based on a position of the first robotic arm, the second torque value indicative of a gravitational component of the torque between the at least two linkages, determine a first force at the IDM based on a difference between the first and second torque values, and determine whether the first robotic arm has collided with an object based on the first force at the IDM.

In another aspect, there is provided a non-transitory computer readable storage medium having stored thereon instructions that, when executed, cause at least one computing device to: measure a first torque value at a joint of a first robotic arm based on an output of a torque sensor, the first robotic arm comprising: two linkages connected by the joint, a torque sensor configured to detect torque between the two linkages, and an instrument device manipulator (IDM) connected to a distal end of the first robotic arm; determine a second torque value at the joint based on a position of the first robotic arm, the second torque value indicative of a gravitational component of the torque between the two linkages; determine a first force at the IDM based on a difference between the first and second torque values; and determine whether the first robotic arm has collided with an object based on the first force at the IDM.

In yet another aspect, there is provided a method of positioning a first robotic arm, comprising: measuring a first torque value at a joint of a first robotic arm based on an output of a torque sensor, the first robotic arm comprising: two linkages connected by the joint, a torque sensor configured to detect torque between the two linkages, and an instrument device manipulator (IDM) connected to a distal end of the first robotic arm; determining a second torque value at the joint based on a position of the first robotic arm, the second torque value indicative of a gravitational component of the torque between the two linkages; determining a first force at the IDM based on a difference between the first and second torque values; and determining whether the first robotic arm has collided with an object based on the first force at the IDM.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
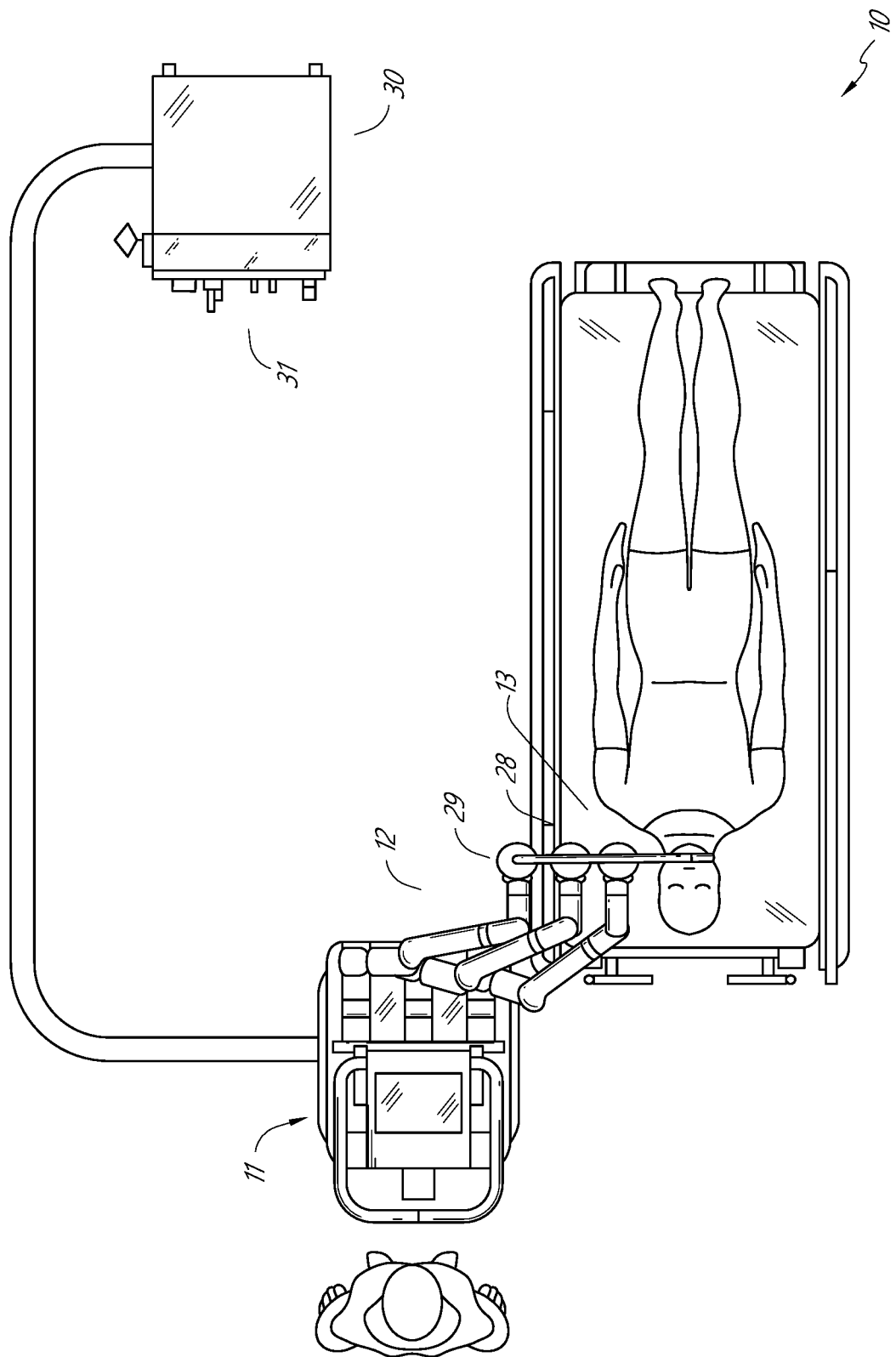
FIG. 1 illustrates an embodiment of a cart-based robotic system arranged for diagnostic and/or therapeutic bronchoscopy procedure(s).
Figure 2:
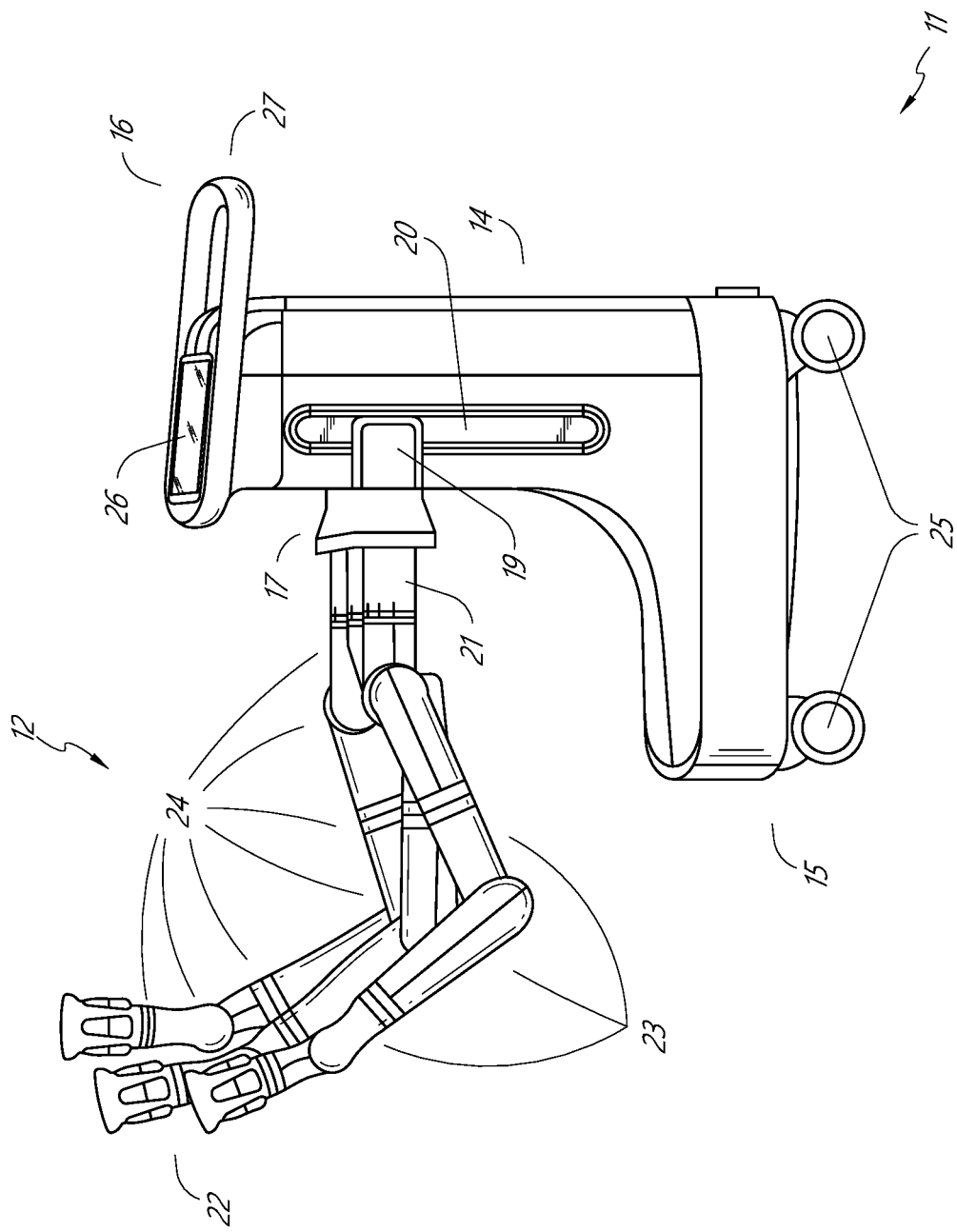
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position the physician may view the console 16, robotic arms 12, and patient while operating the console 16 from behind the cart 11. As shown, the console 16 also includes a handle 27 to assist with maneuvering and stabilizing cart 11.

Figure 3:
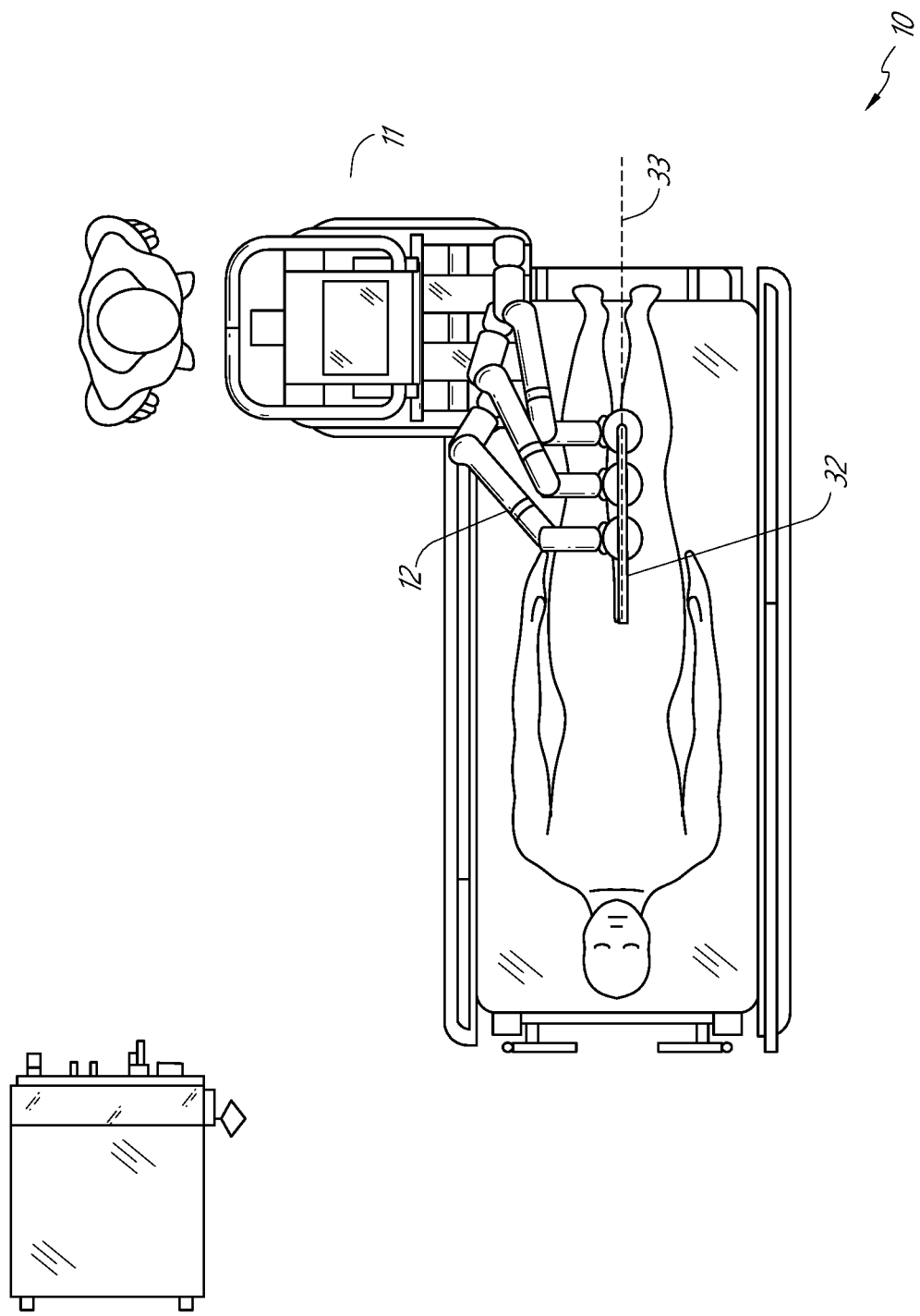
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
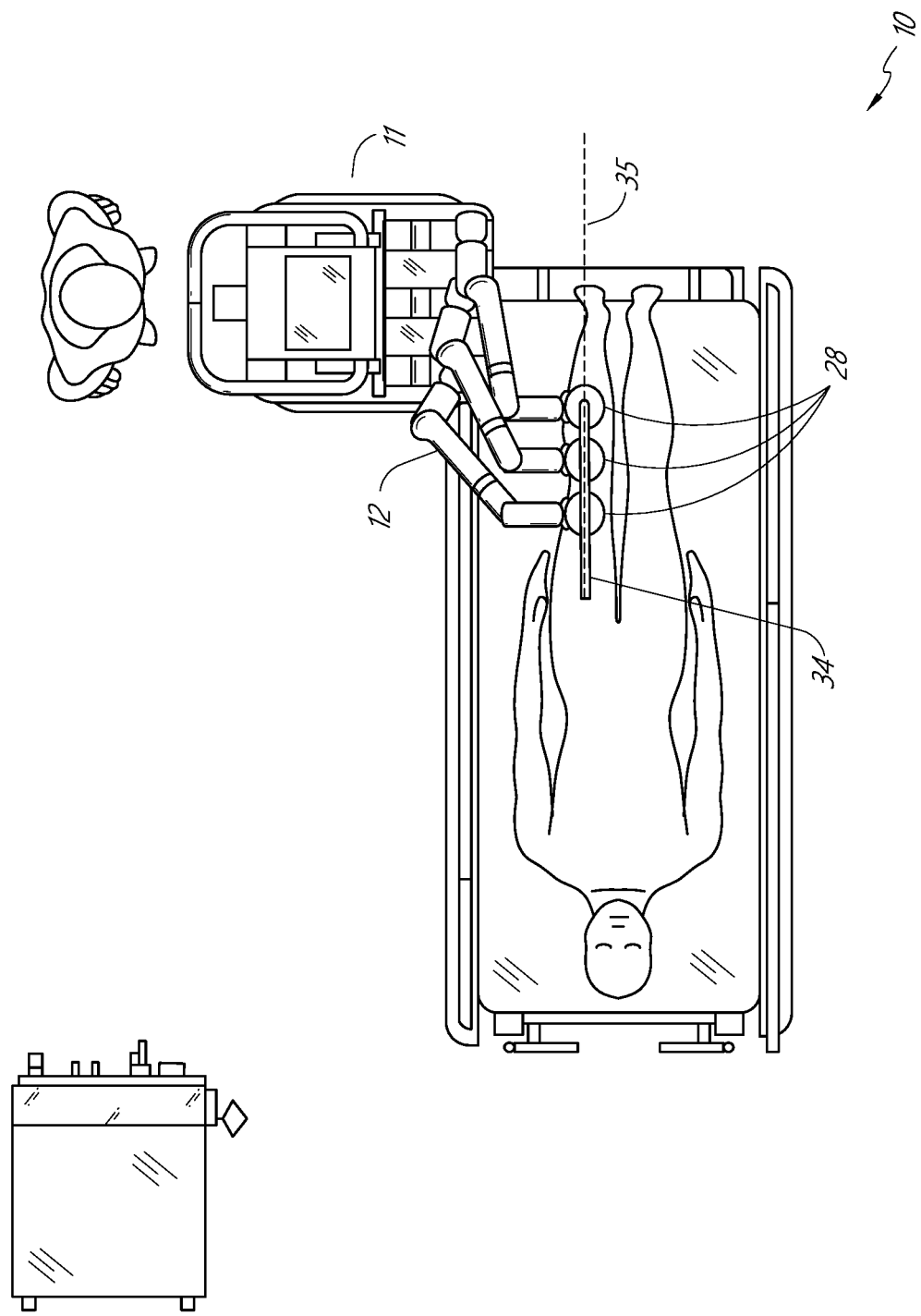
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
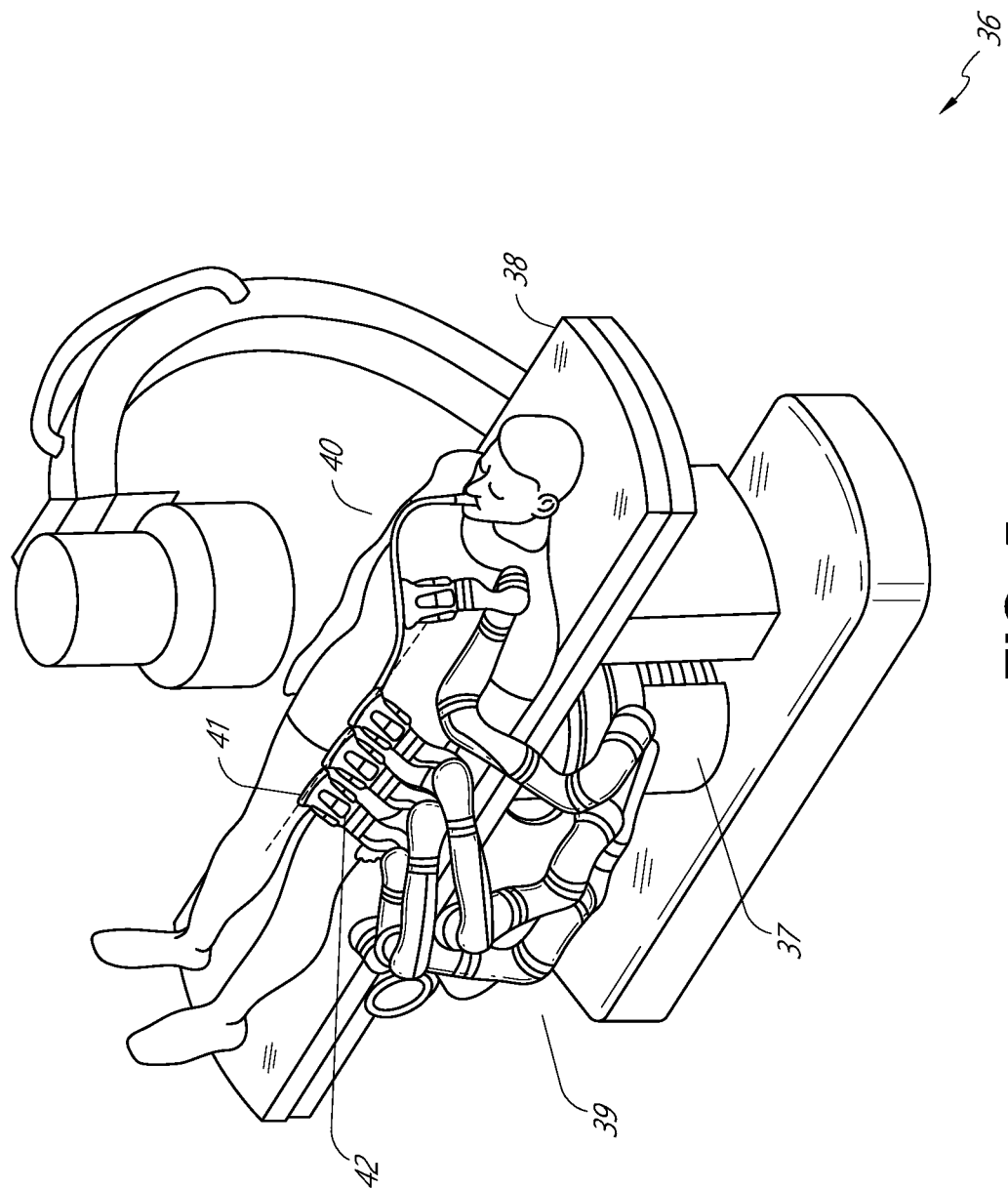
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
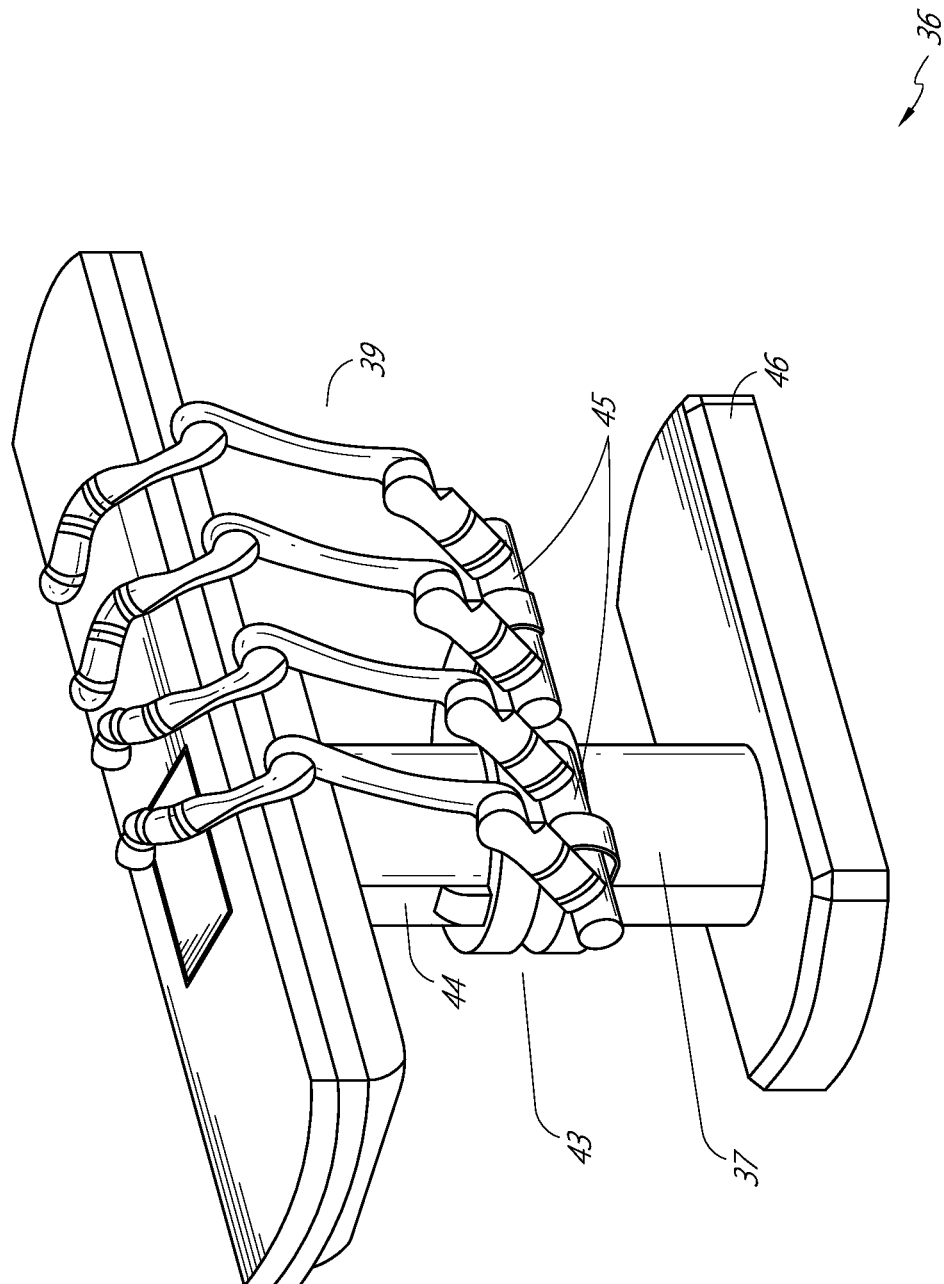
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
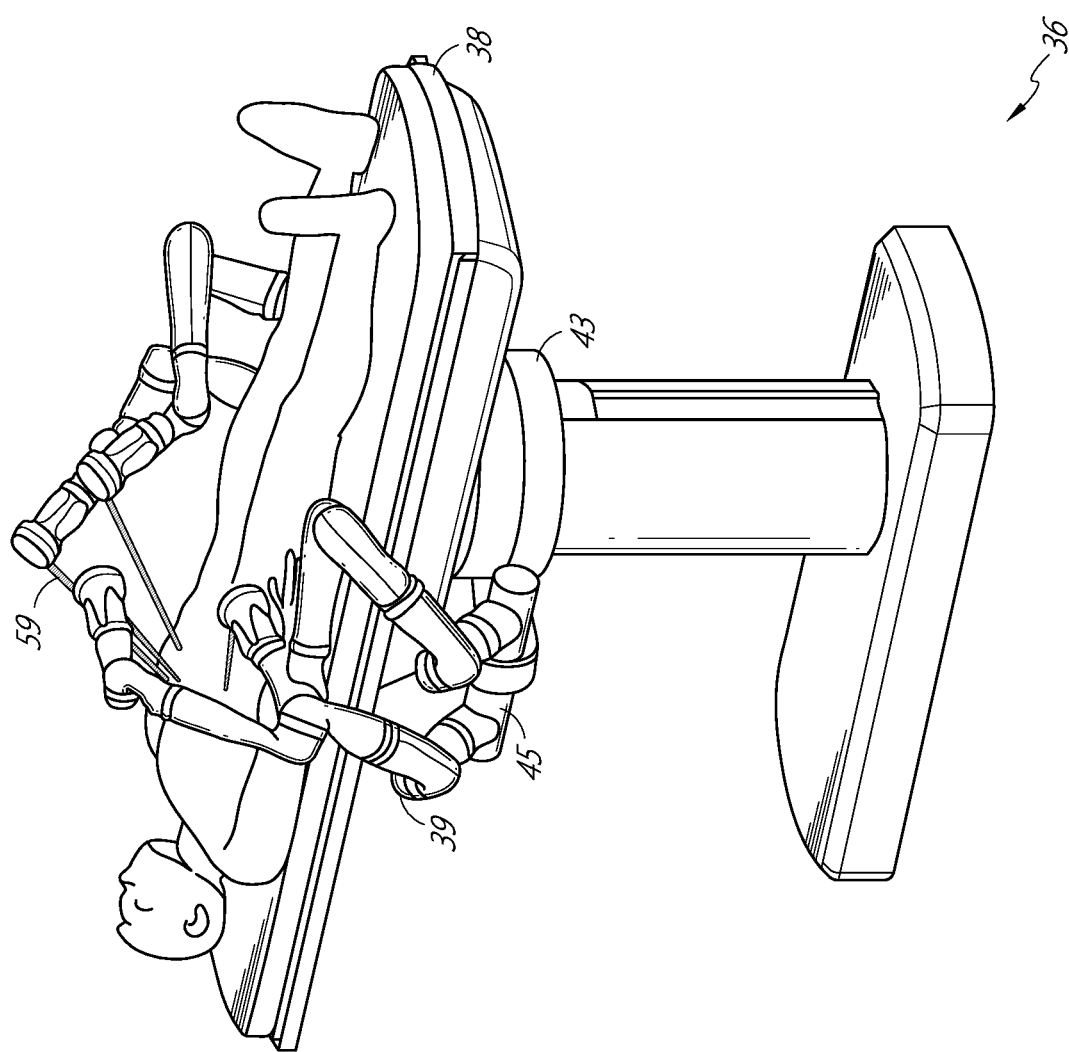
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may be provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
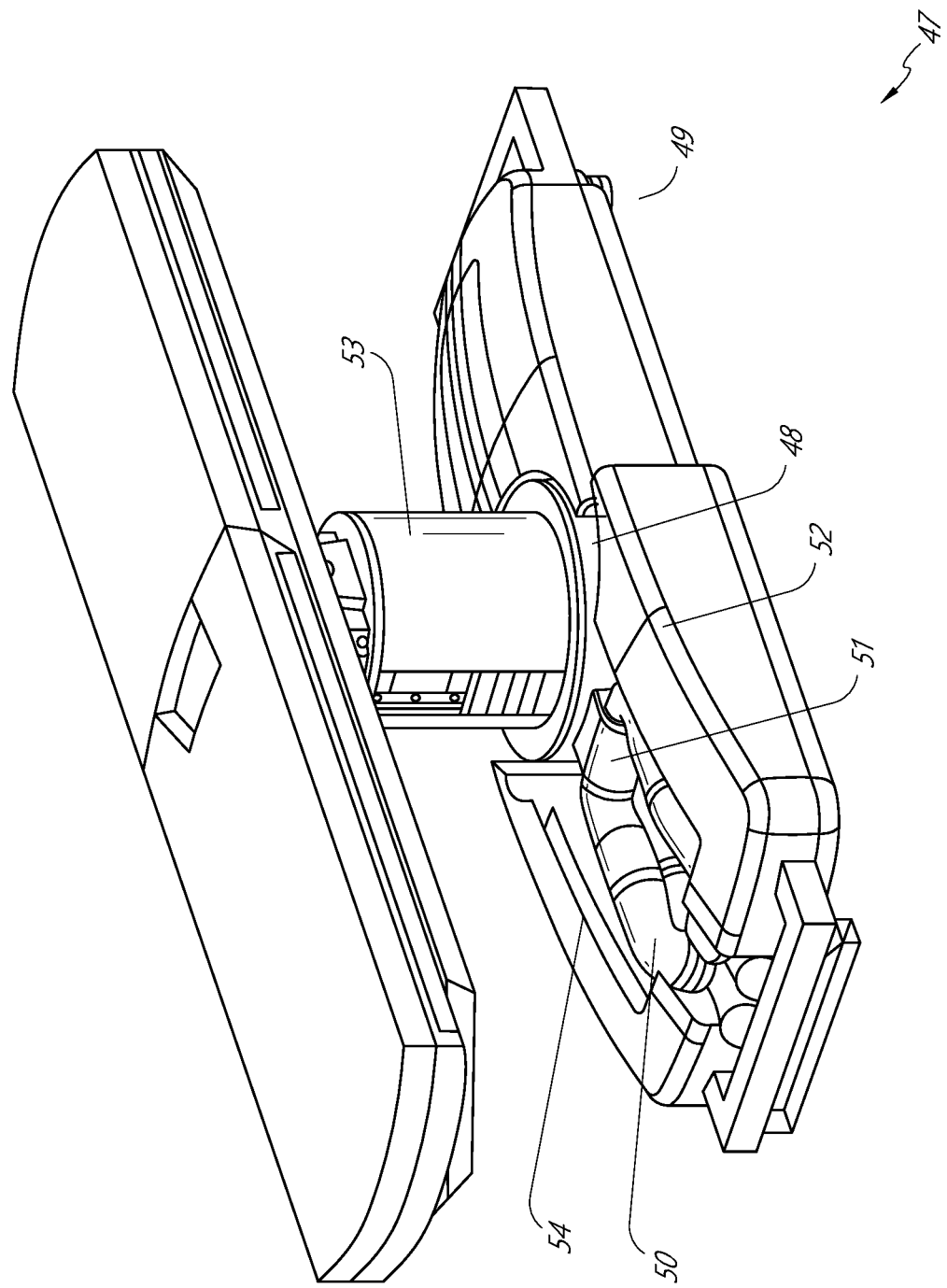
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
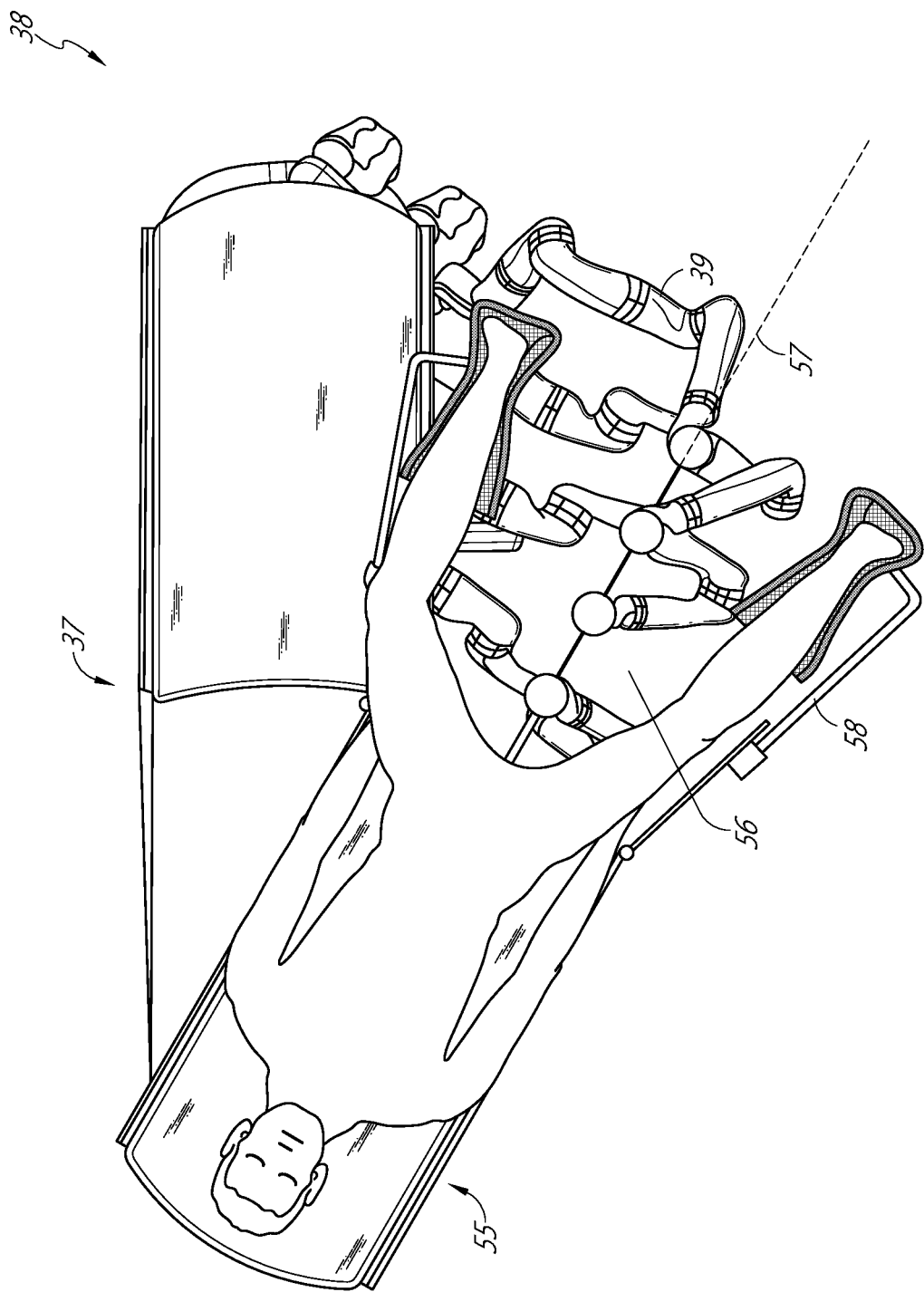
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
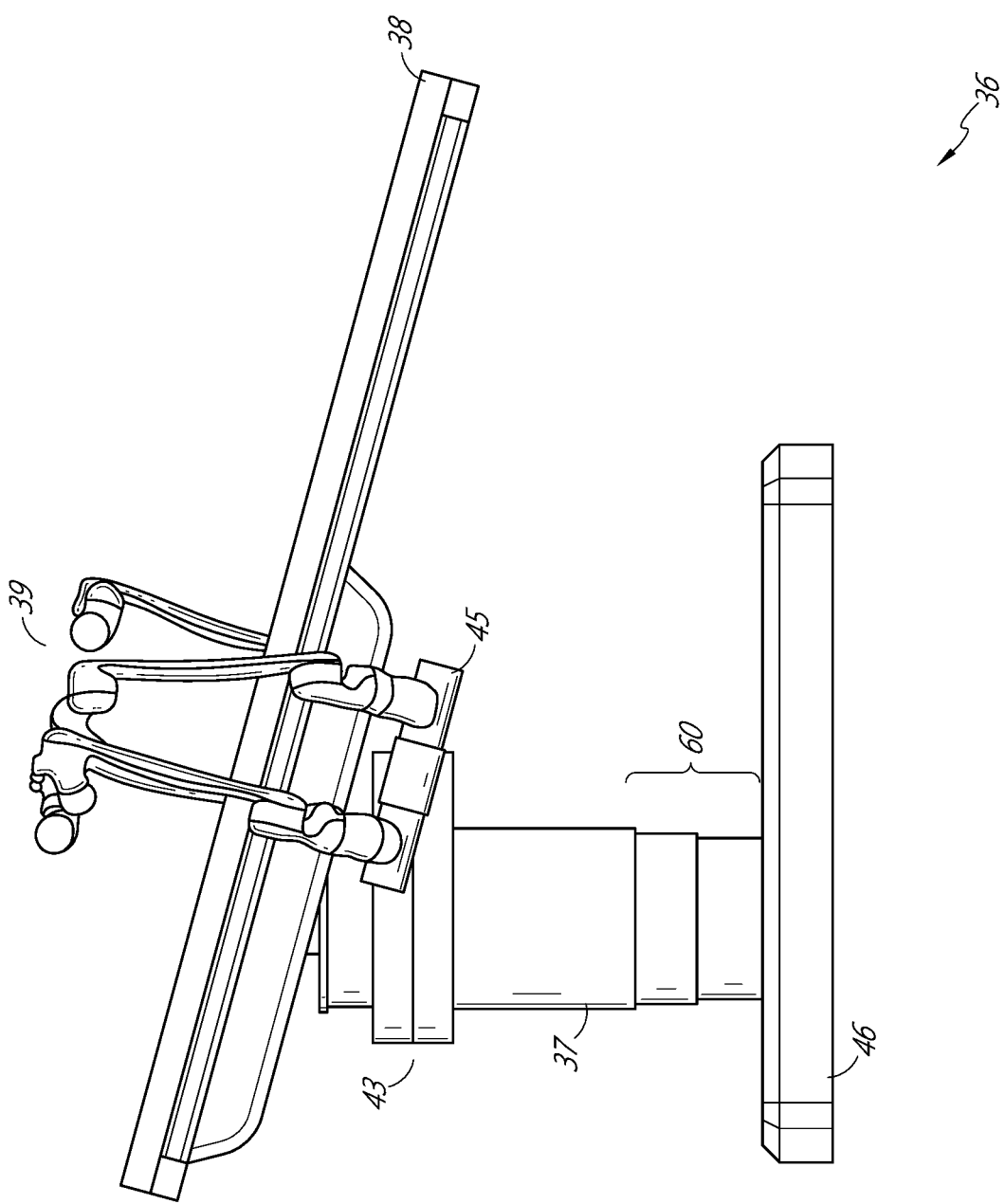
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
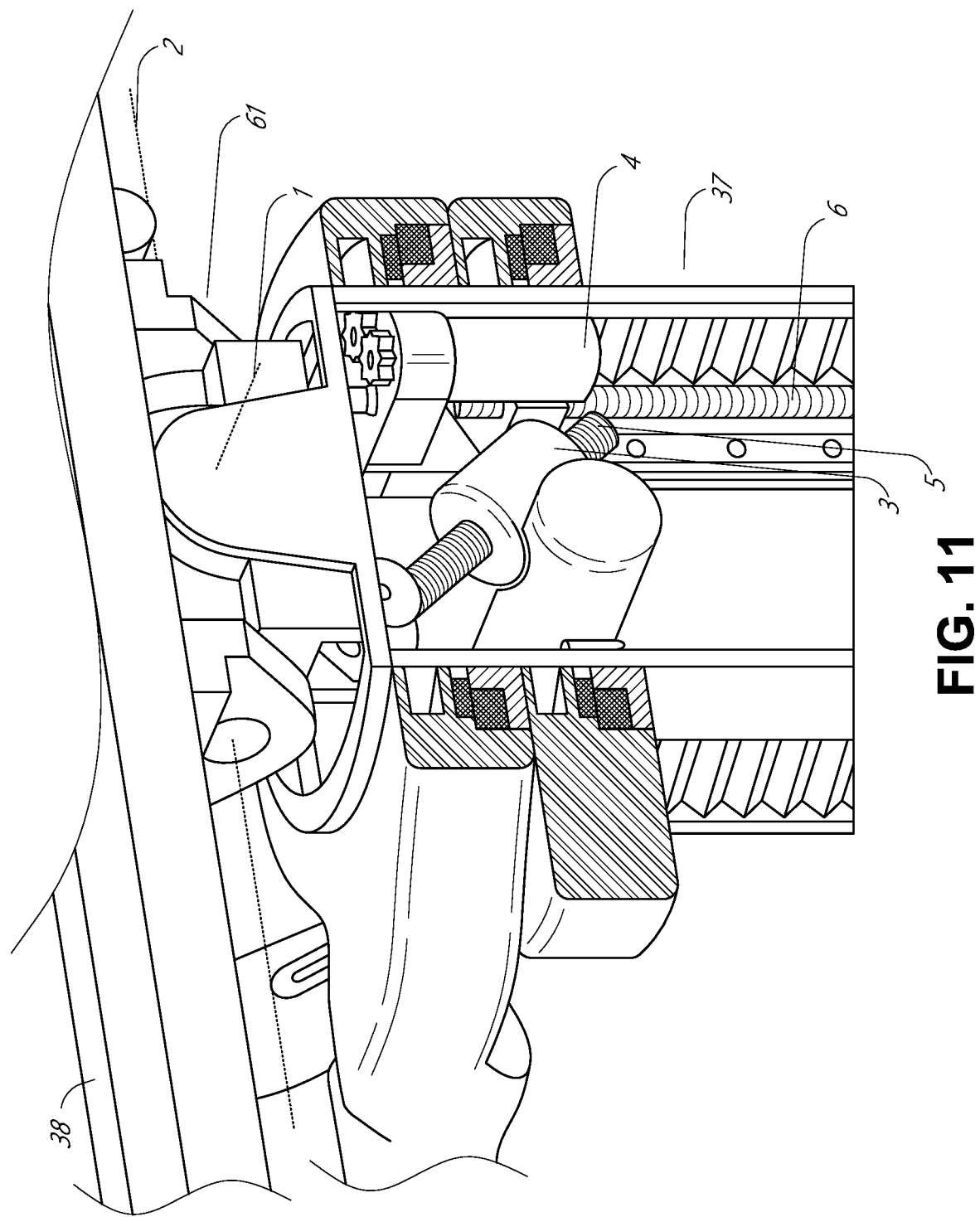
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator" (IDM)) that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
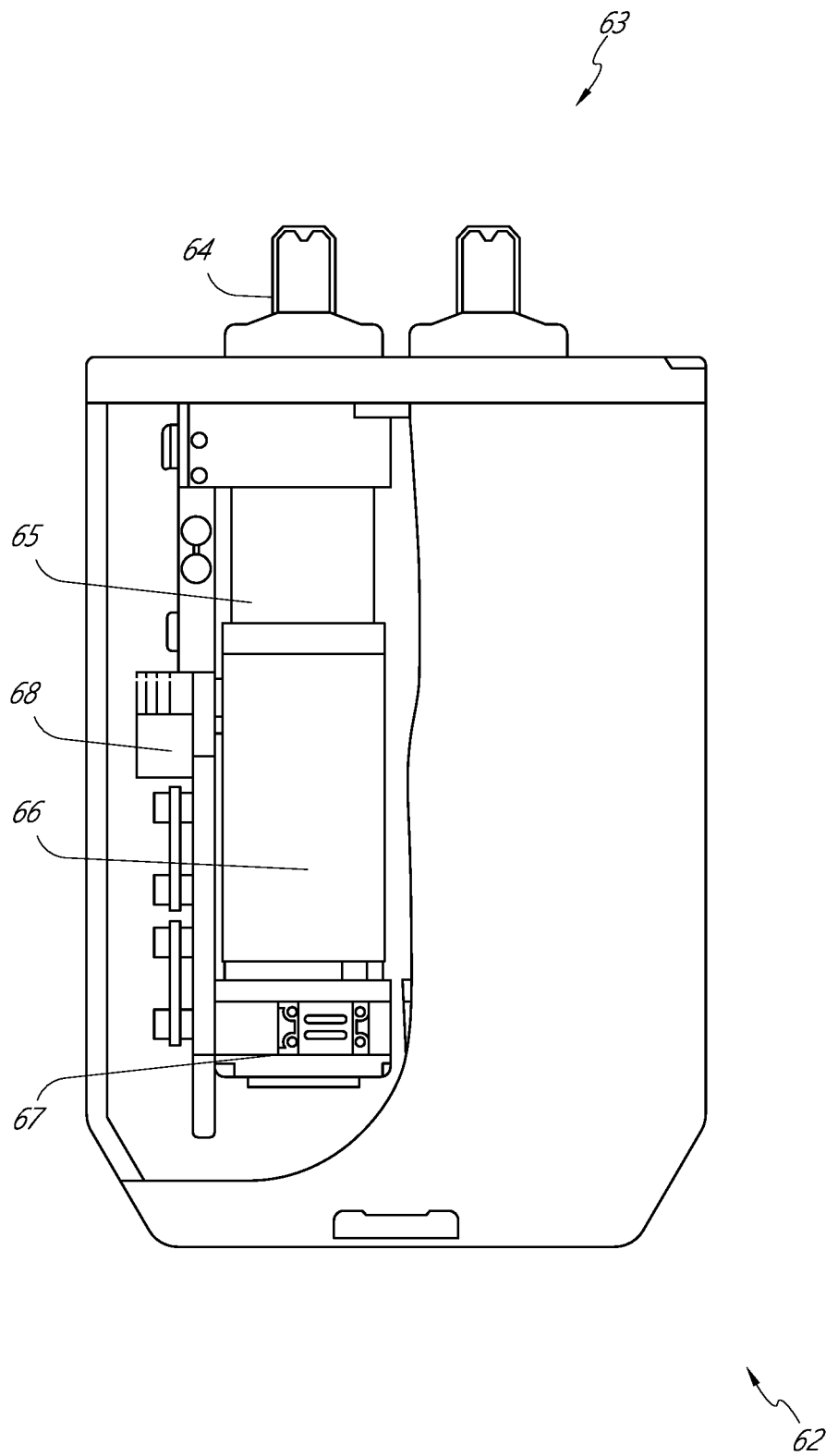
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
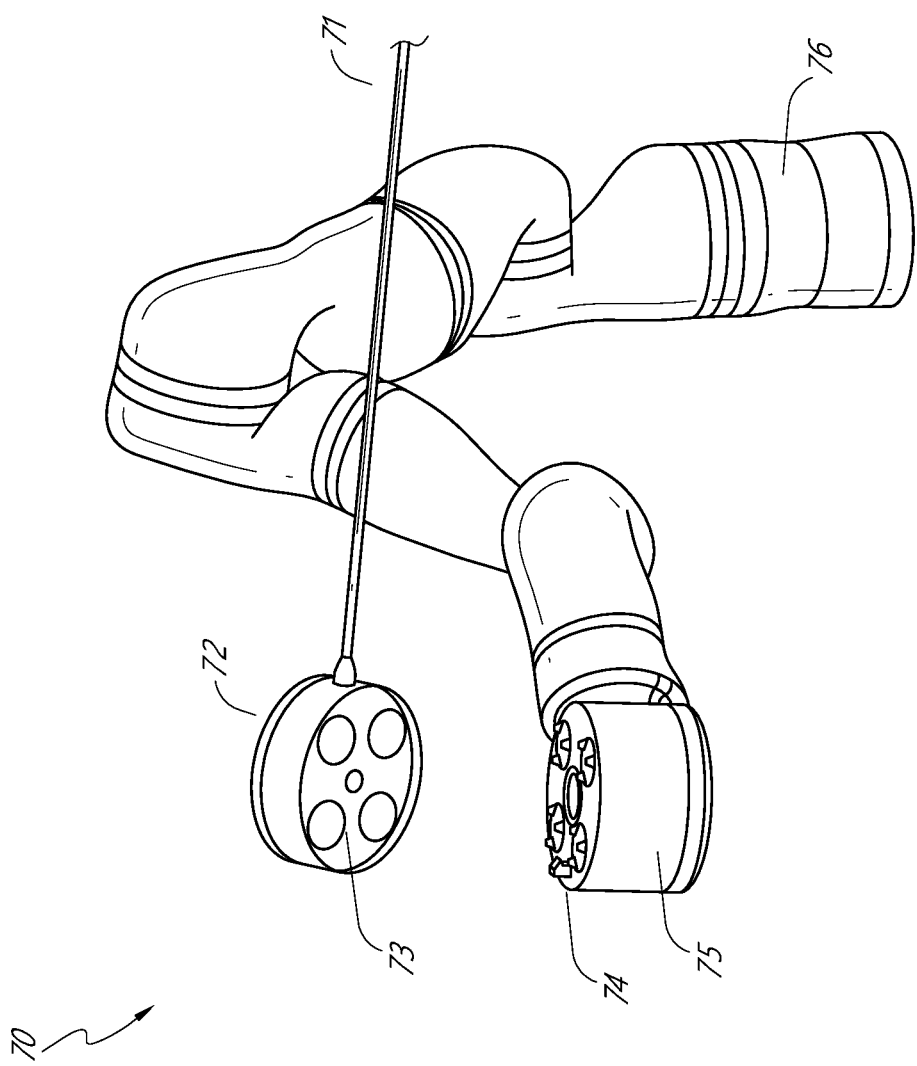
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
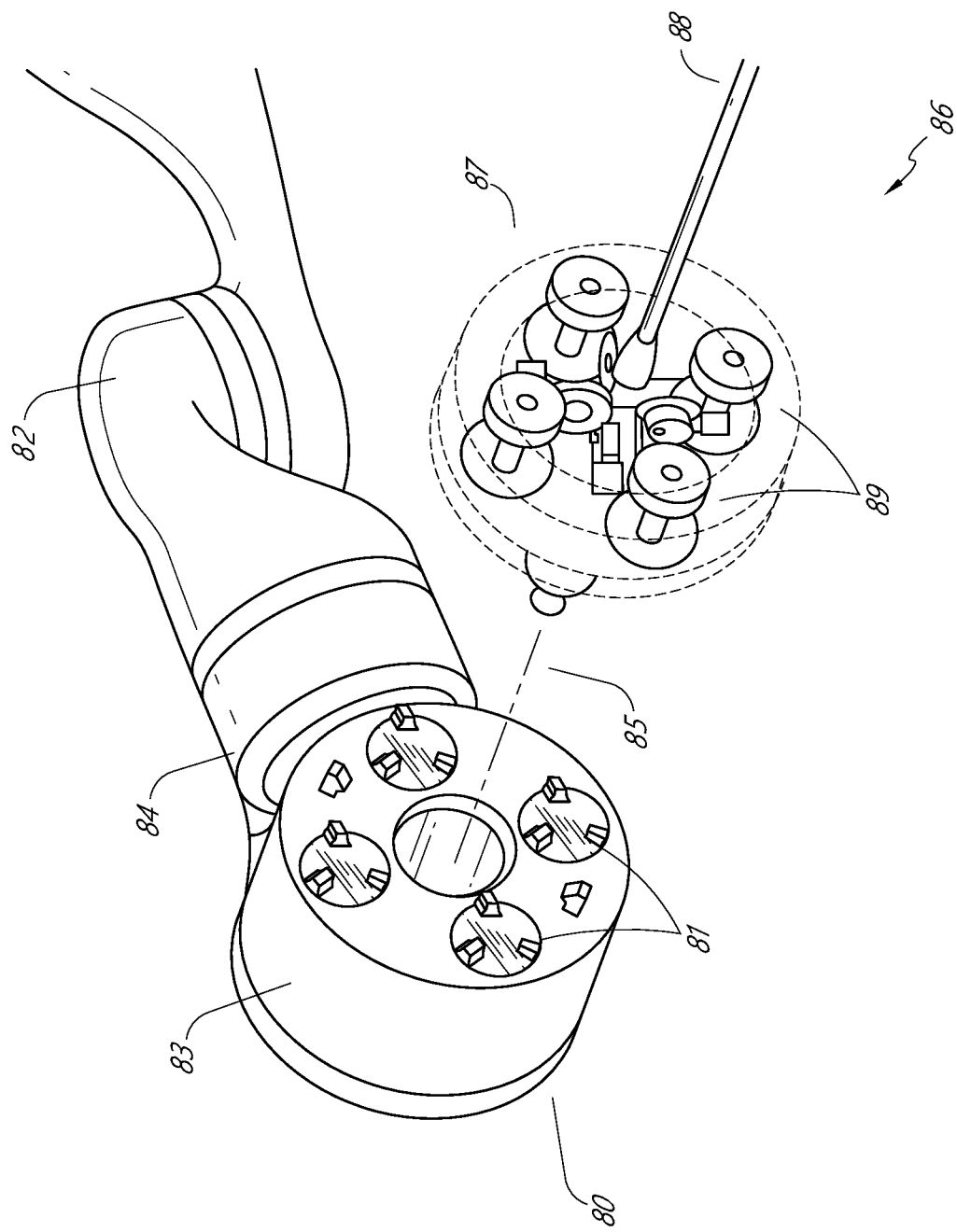
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
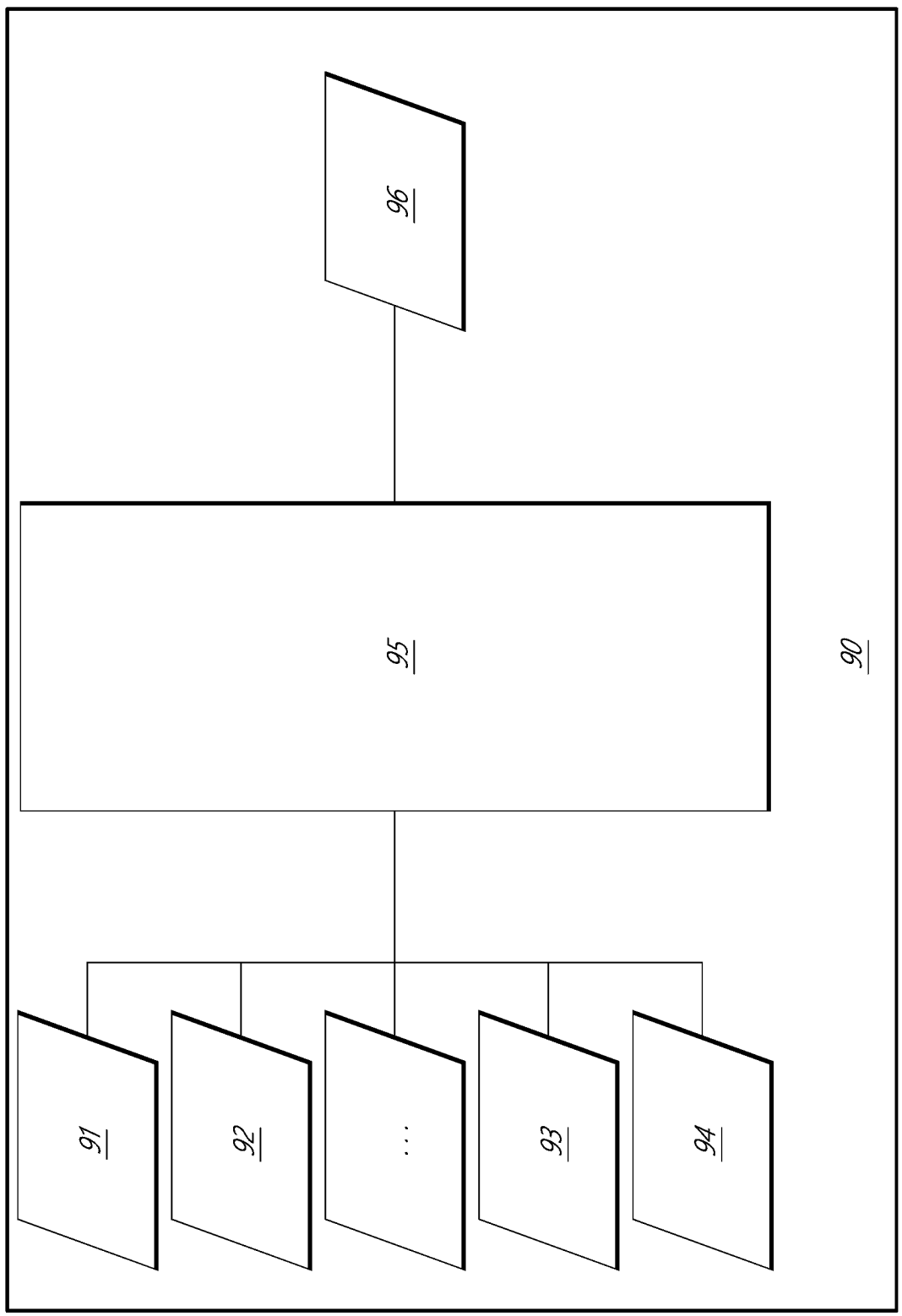
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans generate two-dimensional images, each representing a "slice" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Techniques for Robotic Arm Collision Detection.

Embodiments of the disclosure relate to systems and techniques for the detection of undesirable forces occurring with respect to one or more robotic arms of a surgical robotic system. The detection of undesirable force events may be an important factor in the overall safety of the surgical robotic system. For example, if a robotic arm collides with an object during a medical procedure, the collision may result in unexpected forces being applied to the robotic arm, which may affect the position and/or force applied to a steerable instrument located in the patient. Thus, it is important to detect robotic arm collisions and appropriately respond to the collisions to prevent harm to the patient.

As used herein, the term "collision" may generally refer to contact between two or more objects. A collision may occur between two robotic arms and/or between a robotic arm and another object in the operating environment (e.g., a platform, a cart, a C-arm, etc.). Another source of unexpected or undesirable force(s) at one or more robotic arms may also be misalignment between two robotic arms. While misalignment may not involve a collision between the two robotic arms, misalignment may result in similar unexpected forces, and thus it may also be important to detect misalignment for the overall safety of the surgical robotic system.

The system may take one or more actions in response to the detection of a collision or misalignment. For example, the system may provide an indication of the detected event (e.g., collision or misalignment) to a user of the system. The indication of the detected event to the user may be provided via one or more output devices, including a display device, a haptic feedback device, an audio device, etc. The system may also discontinue the medical procedure until the collision or misalignment event has been resolved.

A. Example System for Detecting Collision and Misalignment.

Figure 16:
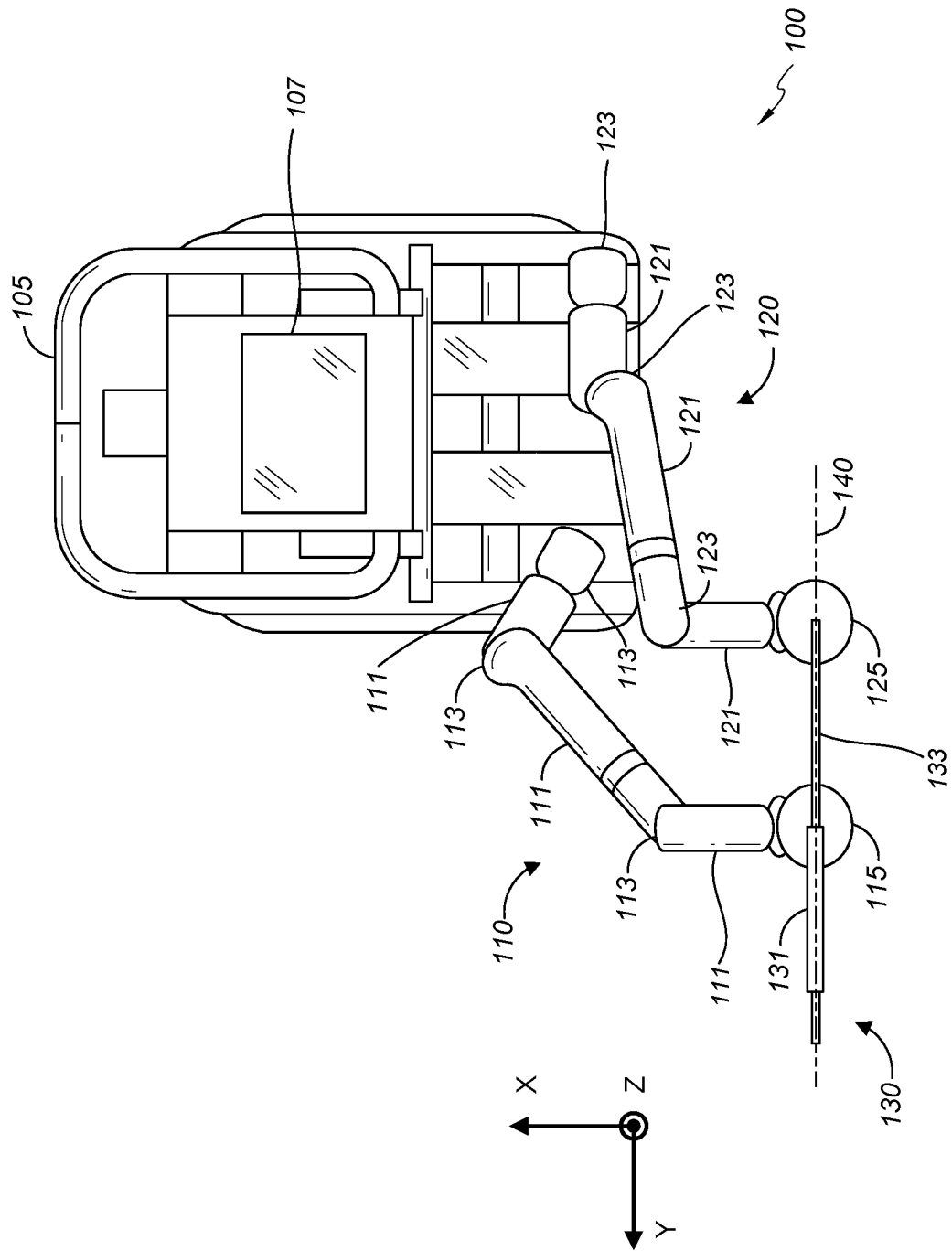
FIG. 16 illustrates an embodiment of a cart-based robotic system which may be configured to detect robotic arm collision in accordance with aspects of this disclosure.

FIG. 16 illustrates an embodiment of a cart-based surgical robotic system which may be configured to detect robotic arm collision and/or misalignment in accordance with aspects of this disclosure. Although FIG. 16 is directed to an embodiment in which the robotic arm(s) are attached to a cart, this disclosure is not limited thereto, and the techniques described herein are be applicable robotic arm(s) which may be attached to a column supporting a patient platform as shown in FIG. 6.

Returning to FIG. 16, provided is a system 100 that may include a cart 105, one or more robotic arm(s) 110 and 120, and a steerable instrument 130. The cart 105 may include a processor (not illustrated), a memory (not illustrated), and a display 107 configured to render encoded data indicative of a detected collision and/or misalignment event. However, depending on the embodiment, one or more of the processor, the memory, and the display 107 may be located on or within another device, such as on the moveable tower 30 illustrated in FIG. 1. Additionally, in other implementations, a feedback device other than the display 107 may be used in place of, or in addition to, the display 107. Other feedback devices which may be employed include haptic devices, speakers, force-feedback actuated via one or more of the robotic arm(s) 112, one or more light-emitting diode(s) LED(s), etc.

The robotic arm(s) 110 and 120 may include a first robotic arm 110 and a second robotic arm 120, respectively. However, aspects of this disclosure are also applicable to system having a greater or fewer number of robotic arms. In the embodiment of FIG. 16, the first robotic arm 110 includes a plurality of linkages 111, a plurality of joints 113, and an IDM 115. Each of the joints 113 connects two adjacent linkages 111. Although not illustrated, the first robotic arm 110 may also include a torque sensor configured to detect torque between two of the linkages 111. In certain implementations, a given joint 113 may house a corresponding torque sensor configured to detect torque between the two linkages 111 adjacent to the given joint 111. A torque sensor may also be provided in the joint 113 that connects the first robotic arm 110 to the cart 105. In certain implementations, the torque sensor(s) may be implemented via a plurality of strain gauges configured to minimize the effects of torques that are not along the axis of rotation of the corresponding joint 113 from affecting the output of the torque sensor.

Additionally, a given joint 113 may further house a motor (not illustrated) configured to apply a force between the two adjacent linkages 111 to the given joint 113 in order to adjust the positioning of the two adjacent linkages 111. The IDM 115 may be connected to a distal end of the robotic arm 110. By actuating the motor(s) in one or more of the joints 113 of the first robotic arm 110, the motor(s) may be operable to adjust the posture or pose of the first robotic arm 110, and thus the IDM 115 (e.g., by adjusting the position and/or orientation of one or more joints 113 of the first arm) and thereby control a steerable instrument 130 attached to the IDM 115.

Each of the joints 113 may further house a position sensor configured to measure the relative position of the two adjacent linkages 111. Thus, a given joint 113 may further house the position sensor, which may be configured to measure the angle between the two adjacent linkages 111. The system may be able to determine the position of each of the linkages 111 in the first robotic arm 110 based on the output of each of the position sensors. Additionally, as discussed below, the output of the position sensors may be used to determine a force applied to a reference point on the first robotic arm 110. In certain embodiments, a given position sensor may include an encoder. The encoder may be configured to measure the speed and/or position of the motor shaft by reading, for example, coded visual information printed on the motor shaft and may provide feedback to the system representative of the speed and/or position of the motor.

Similar to the first robotic arm 110, the second robotic arm 120 may include a plurality of linkages 121, a plurality of joints 123 connecting adjacent linkages 121, and an IDM 125. Each of the joints 123 may house a corresponding torque sensor and motor (not illustrated). The IDM 125 may also be attached to the second medical instrument 133 to operate the steerable instrument 130.

In certain embodiments, rather than including separate torque sensors and motors in each of the joints 113 and 123, the motors may also function as torque sensors. For example, when a force is applied to the first robotic arm 110 (e.g., the force of gravity, the force of a collision, a force exerted by a user, etc.), the motor(s) may be configured to apply opposite and opposing force(s) to the joint 113 to maintain the position of the first robotic arm 110. The current required in the motor(s) to maintain the first robotic arm 110 position may correspond to the torque applied to the corresponding joints 113.

The steerable instrument 130 in the FIG. 16 embodiment comprises a first medical instrument 131 attached to the IDM 115 of the first robotic arm 110 and a second medical instrument 133 attached to the IDM 125 of the second robotic arm 120. However, the illustrated example in FIG. 16 is merely one example steerable instrument 130 and other embodiments may include a steerable instrument 130 that is controlled by a single robotic arm 110 or a steerable instrument 130 that requires three or more robotic arms for operation. Depending on the embodiment and the medical procedure being performed, each of the first and second medical instruments may comprise one of an inner leader portion, an outer sheath portion, a needle, forceps, a brush, etc.

The first and second medical instruments 131 and 133 may be configured to be advanced/inserted into (or retracted from) a patient along a first axis 140. As discussed above, the first axis 140 may be termed a virtual rail. The virtual rail may be defined by the axis of alignment of the IDMs 115 and 125. Movement of the IDMs 115 and 125 along the virtual rail may control the advancing and retracting of the first and second medical instruments 131 and 133 into and out of the patient. As shown in FIG. 16, a coordinate system may be defined with respect to the first axis 140. For example, the first axis 140 (e.g., the virtual rail or axis of insertion) may be defined along a Y-axis, the Z-axis may be defined based on the direction of gravity (e.g., substantially perpendicular to the first axis 140), and the X-axis may be selected perpendicular to the Y-Z plane. However, depending on the procedure, the axis of insertion 140 may not correspond to a horizontal axis perpendicular to the direction of gravity. The coordinate system of the robotic arms may be selected in any manner without departing from the scope of this disclosure.

B. Determination of Force Applied to Robotic Arm(s) and Collision Detection.

One technique for detecting collisions or misalignment of the robotic arm(s) is to analyze the forces experience by the robotic arm(s). For example, while the robotic arm(s) are stationary, the only expected force on the arm(s) is the force due to gravity. Accordingly, any force experienced by the robotic arm(s) that is inconsistent with the expected force due to gravity (e.g., when the difference between the expected force and the measured force is greater than a threshold value) may be indicative of a collision between at least one of the robotic arm(s) and another object.

Certain surgical robotic systems may incorporate a force sensor in each of the robotic arms to measure the force experienced at a reference point on the corresponding robotic arm. For example, a force sensor may be positioned on or near (e.g., within a defined distance of) the IDM 115 of the first robotic arm 110 of FIG. 16 to measure the forces applied to the IDM 115. However, force sensors that are able to directly measure the applied force at the IDM 115 (e.g., the force sensor is located at the IDM 115) with the required accuracy may be relatively costly. Thus, in certain implementations, the system may determine the force at the IDM 115 (or any reference point on the robotic arm 110) using torque values output from the torque sensors located within the joints 113.

Figure 17:
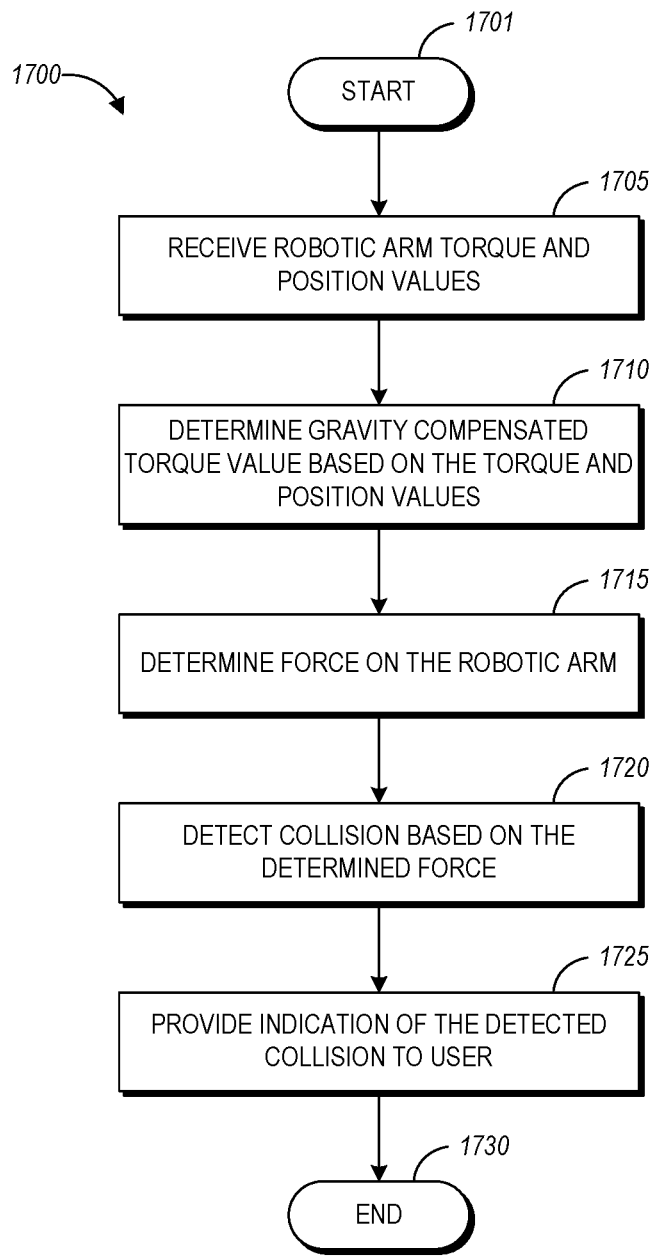
FIG. 17 is a flowchart which illustrates an example procedure for determining a force applied to a robotic arm and detecting a collision in accordance with aspects of this disclosure.

FIG. 17 is a flowchart which illustrates an example procedure for determining a force applied to a robotic arm and detecting a collision in accordance with aspects of this disclosure. The method 1700 illustrated in FIG. 17 is merely an example implementation and the method 1700 may be modified by adding, removing, and or modifying one or more of the blocks associated with the method 1700. For convenience, method 1700 will be described as being performed by a system (e.g., the surgical robotic system 100 of FIG. 16). However, certain aspects of the method 1700 may be performed, for example, by one or more processors of the system based on computer-executable instructions stored in memory. Further, the method 1700 will be described in connection with a single robotic arm. However, a similar method may be performed to determine the force experienced by multiple robotic arms included in the system.

The method 1700 begins at block 1701. At block 1705, the system receives robotic arm torque and position values. The system may receive torque values from each of the torque sensors included in the robotic arm. Further, the system may retrieve position values from position data stored in memory that indicate the position of each of the linkages in the robotic arm. For example, the robotic arms may further include an encoder formed on each of the joints. The encoder may measure the speed and/or position of the motor shaft by reading coded visual information printed on the motor shaft and may provide feedback to the system representative of the speed and/or position of the motor. The system may be configured to determine the position of each of the joints based on the feedback from the encoders. Using the information from each of the encoders positions on the robotic arm, the system can determine to position of each of the linkages and the IDM.

At block 1710, the system determines a gravity-compensated torque value for each of the joints based on the torque values and position values. The gravity-compensated torque value for a given joint may represent the component of the torque at the joint that is due to forces other than the force of gravity. In one implementation, the system may measure a first torque value at a joint based on the output of the corresponding torque sensor. The system may then determine a second torque value at the joint based on the position of the robotic arm. The position data of the robotic arm may include data that enables the system to determine the position of the two linkages connected by the joint and the angle formed therebetween. The second torque value may be indicative of a gravitational component of the torque between the two linkages. The system may then be able to determine the gravity-compensated torque value based on the first and second torque values. For example, the difference between the first and second torque values may correspond to the gravity-compensated torque value.

At block 1715, the system may determine the force exerted on the robotic arm based on the gravity-compensated torque values for each of the joints. The determined force may therefore exclude the component of the forces experienced by the robotic arm due to gravity. An example of one technique for determining the gravity-compensated torque value and the force applied at a reference point on the robotic arm will be discussed in connection with FIG. 18 below.

At block 1720, the system may detect a collision based on the determined force. For example, when the force exceeds a threshold value, the system may determine that the robotic arm has collided with another object. In certain implementations, the system may also determine whether the robotic arm is misaligned with another robotic arm based on the determined force. At block 1725, the system may provide an indication of the detected collision to a user of the system. For example, in response to determining that the force exceeds the threshold value, the system may notify the user that a collision has been detected. Further, in response to detecting misalignment, the system may also provide an indication of the detected misalignment to the user. The method 1700 ends at block 1730.

C. Robotic Arm Free-Body Diagram.

Figure 18:
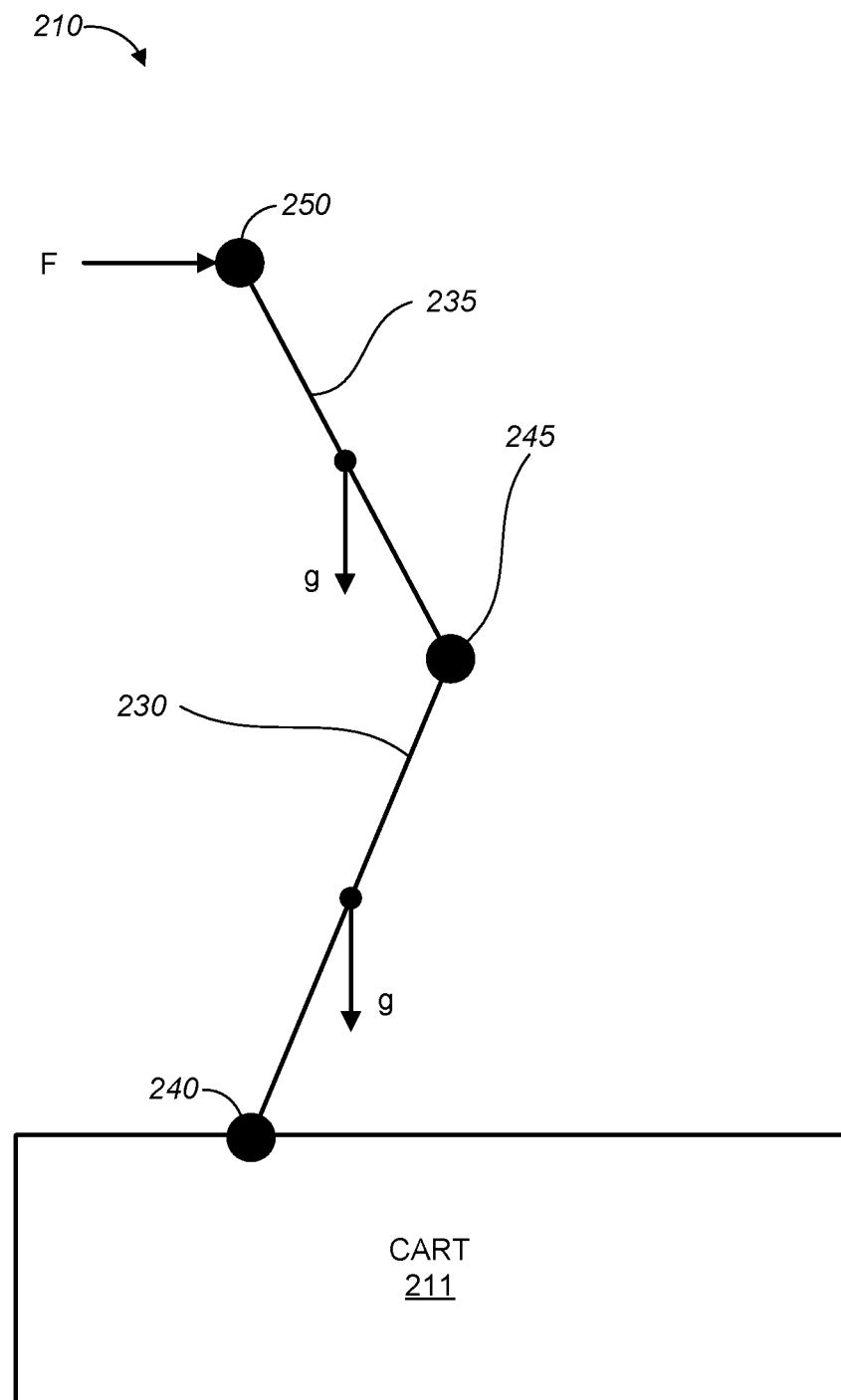
FIG. 18 illustrates a free-body diagram of a robotic arm for describing techniques for calculating forces applied to the robotic arm in accordance with aspects of this disclosure.

FIG. 18 illustrates a free-body diagram of a robotic arm for describing techniques for calculating forces applied to the robotic arm in accordance with aspects of this disclosure. The robotic arm 210 may be attached to a cart 211. The robotic arm 210 may include a first linkage 230, a first joint 240 connecting the first linkage 230 to the cart 211, a second linkage 235, a second joint 245 connecting the first and second linkages 230 and 235, and an IDM 250 connected to the distal end of the second linkage 235. The robotic arm 210 is illustrated in a simplified form in FIG. 18; however, more complex robotic arms may be analyzed in a similar manner by adding additional linkages to the arm connected by additional joints. The IDM 250 may define a reference point at which an external force F is modeled as being applied to the robotic arm 210. However, in other embodiments, the reference point may be set to any other point along the robotic arm 210. Additionally, the force due to gravity experienced by each of the first and second linkages 230 and 235 is illustrated in the diagram as a gravity force vector g applied at the center of gravity of the corresponding linkage 230 and 235.

Each of the joints 240 and 245 may include a torque sensor configured to output a measured torque value $\tau_{measured}$. The measured torque value $\tau_{measured}$ at each of the joints 240 and 245 may be determined according to the following equation:

$$\tau_{measured} = \tau_{force} + \tau_{gravity} \quad (1)$$

where $\tau_{measured}$ is the measured torque value, $\tau_{force}$ is the torque at the joint 240 or 245 due to the force F applied to the robotic arm 210, and $\tau_{gravity}$ is the torque applied to joint 240 or 245 due to the force of gravity g. In this embodiment, the force F applied to the robotic arm 210 is modelled as being applied to the IDM 250 as a reference point. However, the force may be modelled as being applied to the robotic arm 210 at difference points depending on the embodiment.

The torque due to the force F applied at the reference point and the torque due to gravity g may be determined as follows:

$$\tau_{force} = J(\theta)^T F \quad (2)$$

$$\tau_{gravity} = G(\theta, g) \quad (3)$$

where $J(\theta)^T$ is a Jacobian transpose matrix that represents the transmission of the force F to the joint 240 or 245 based on the positions of the joints 240 or 245 in the robotic arm 210 and $G(\theta, g)$ represents the transmission of torque to the joints 240 or 245 due to gravity g. Substituting equations (2) and (3) into (1) gives:

$$\tau_{measured} = J(\theta)^T F + G(\theta, g) \quad (4)$$

Accordingly, the force F applied to the reference point (e.g., the IDM 250) can be solved based on the measured torques $\tau_{measured}$, the Jacobian transpose matrix $J(\theta)^T$, and the transmission of torque due to gravity $G(\theta, g)$.

D. Collision and Misalignment Detection.

Once the force(s) at a reference point on one or more robotic arms have been determined, the system may determine whether a collision or misalignment event has occurred based on the force(s). This determination may be based on whether the determined force(s) are consistent with the expected forces at the reference points.

When a robotic arm is stationary, the expected value of a gravity-compensated force (e.g., the determined force in which the component of the force due to gravity has been removed) is zero. That is, under normal circumstances, there is no force expected to be applied to the arm other than the force due to gravity when the robotic arm is stationary. As such, when the robotic arm is stationary, the system may compare the force to a threshold value. If the gravity-compensated force is greater than the threshold value, the system may determine that an object has collided with the robotic arm.

In certain implementations, the system may determine the components of the force in each of the X, Y, and Z-axes. The system may, at a certain frequency, determine the components of the force during a medical procedure. The expected values of the force may depend on the medical procedure being performed. For example, while a medical instrument is being advanced into a patient along the Y-axis (which may correspond to a first axis 140 or axis of insertion, see FIG. 16), the IDM may experience a resistance to the insertion as a force along the Y-axis. A similar resistance force along the Y-axis may be generated when the medical instrument is retracted from the patient. Thus, forces along the Y-axis during insertion or retraction of the medical device may not necessarily be indicative of a collision. For example, the system may compare the external force direction to the actual insertion direction of the medical instrument to determine whether the force is consistent with normal operation of the robotic arm (e.g., the force is in substantially the same direction as the actual insertion direction) or the force is consistent with collision with an external object (e.g., at least a portion of the force is in a direction other than the actual insertion direction).

Figure 19A:
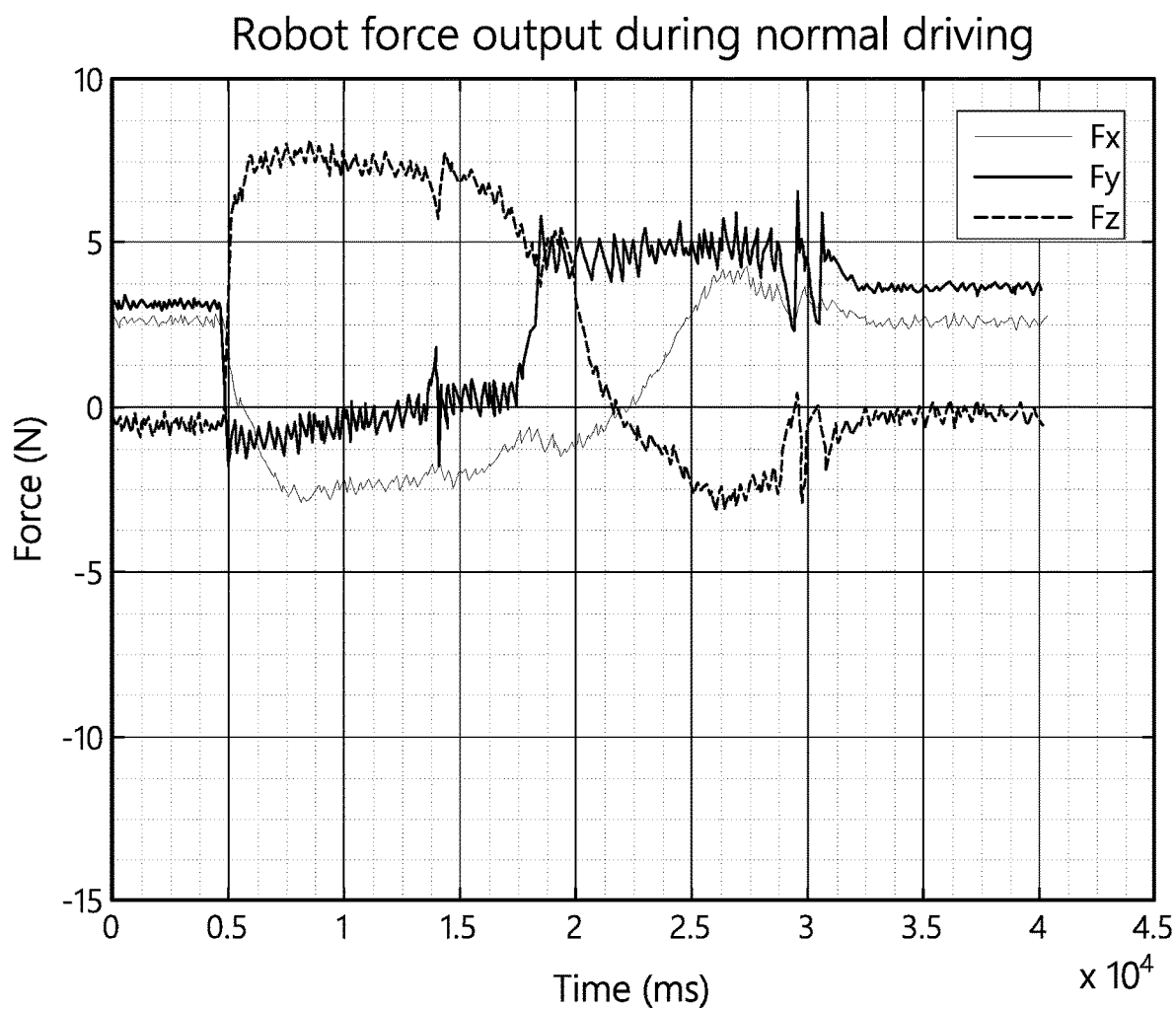
FIG. 19A is a graph illustrating an example of the forces measured during insertion of a medical instrument in accordance with aspects of this disclosure.

FIG. 19A is a graph illustrating an example of the forces measured during insertion of a medical instrument in accordance with aspects of this disclosure. In the example graph, a first instrument is moved/driven by a first robotic arm from 5,000 ms to 18,000 ms and a second instrument is driven by a second robotic arm from 18,000 ms to 34,000 ms. The illustrated X, Y, and Z-components of the force are measured in the second robotic arm. As shown in FIG. 19A, each of the X, Y, and Z-components of the force has a magnitude that is less than 10 N. The Y-axis component of the force measured by the second robotic arm has a value between about 3 N and 5 N during driving of the second medical instrument (e.g., between 18,000 ms and 34,000 ms). The X-axis and Z-axis components of the force may be caused due to minor misalignments (e.g., misalignments within expected tolerances) or due to forces exerted on the medical instrument due to the path taken by the medical instrument within one of the patient's luminal networks which may be transmitted back to the IDM via the medical instrument. The X-axis and Z-axis components of the force may also result from inaccuracy of a model of the effects due to gravity on the second robotic arm based on the second robotic arm's current position.

Additionally, the X and Z-components of the force may be correlated with the Y-component of the force or changes in the configuration of the medical instrument as the medical instrument is being driven. That is, changes in the X and Z-components of the force may occur when driving of the medical instrument starts or stops (e.g., when the Y-component of the force transitions to or from about 0 N). Further, when the direction of insertion of the distal end of the medical instrument changes, the force transmitted back to the IDM from the medical instrument may also change.

Figure 19B:
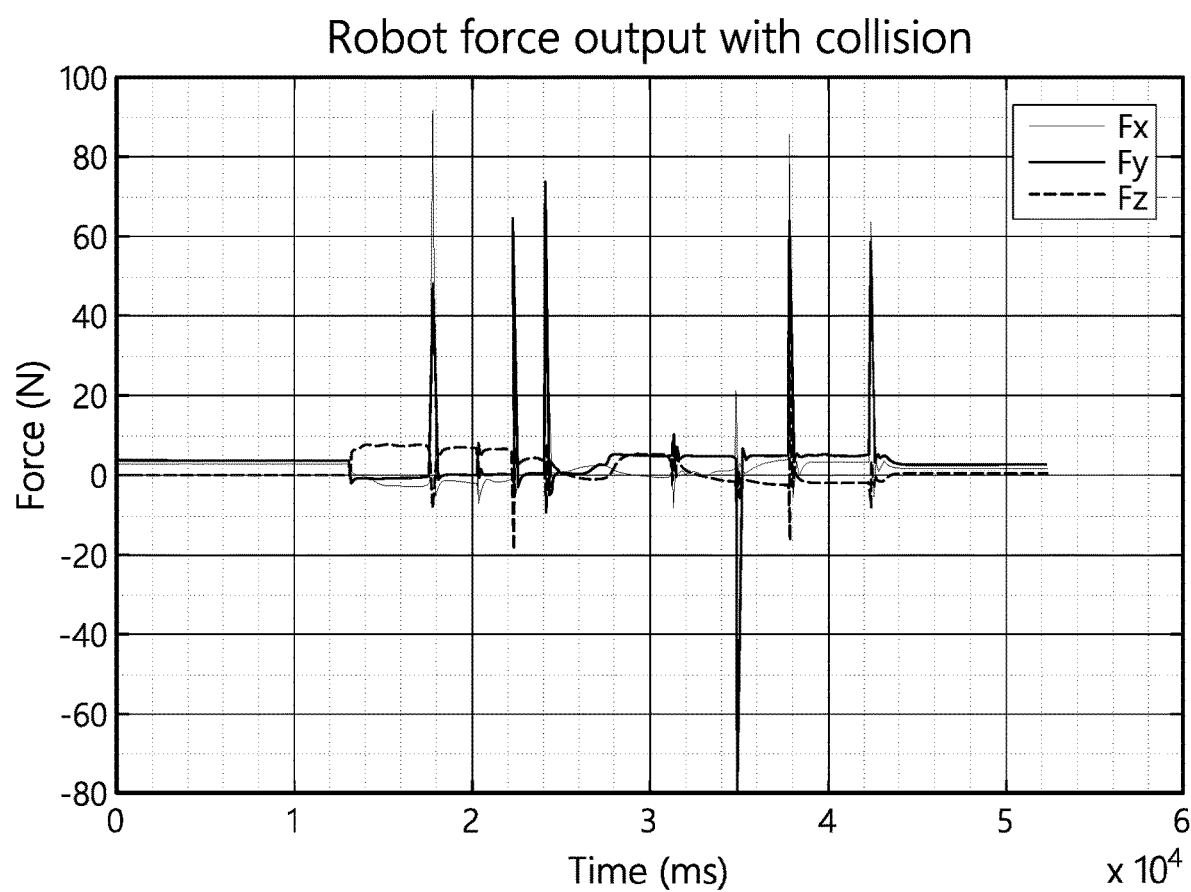
FIG. 19B is a graph illustrating an example of the forces measured during insertion of a medical instrument which may be indicative of a collision event in accordance with aspects of this disclosure.

FIG. 19B is a graph illustrating an example of the forces measured during insertion of a medical instrument which may be indicative of a collision event in accordance with aspects of this disclosure. As shown in FIG. 19B, at least one of the X, Y, and Z-components of the force includes a sharp spike which is consistent with a collision event between the robotic arm and another object. The collision forces may be significantly greater than the forces experienced during normal insertion of the medical instrument. Here, when the system detects that one of the forces is greater than a threshold value, the system may determine that the robotic arm has collided with another object. In FIG. 19B, collision events may be detected by the system at about times 18,000 ms, 22,000 ms, 24,000 ms, 35,000 ms, 38,000 ms, and 42,000 ms.

Figure 19C:
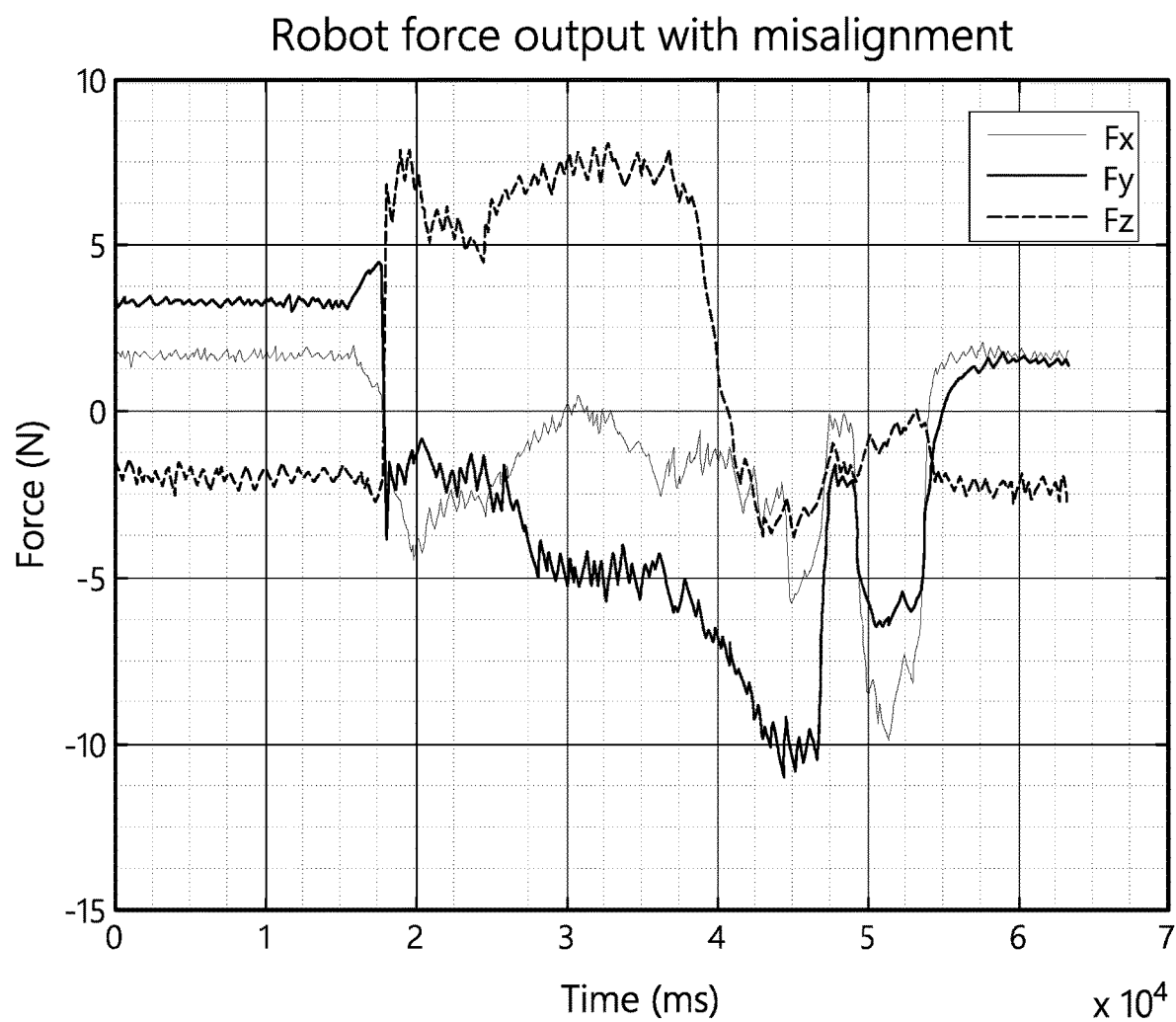
FIG. 19C is a graph illustrating an example of the forces measured during insertion of a medical instrument which may be indicative of a misalignment event in accordance with aspects of this disclosure.

FIG. 19C is a graph illustrating an example of the forces measured during insertion of a medical instrument which may be indicative of a misalignment event in accordance with aspects of this disclosure. As shown in FIG. 19C, changes in the X and Z-components of the force may not be directly correlated with the timing of starting and stopping insertion of the medical instrument into the patient. However, these non-correlated changes may also be consistent with changes in the force transmitted back through the medical instrument (e.g., due to changes in the configuration of the medical instrument). Thus, in certain implementations, the system may be further configured to distinguish between forces caused due to misalignment from expected changes in the X and Z-components of the force which may be consistent with normal driving of the medical instrument.

Referring back to FIG. 16, a medical instrument such as, for example, the steerable instrument 130 may include a first medical instrument 131 attached to a first IDM 115 of the first robotic arm 110 and a second medical instrument 133 attached to a second IDM 125 of the second robotic arm 120. The first medical instrument 131 may define a working channel through which the second medical instrument 133 is configured to be advanced and/or retracted. Accordingly, the first robotic arm 110 may be configured to advance the first medical instrument 131 into the patient along the first axis 140 (e.g., the Y-axis) and the second robotic arm 120 may be configured to advance the second medical instrument 133 into the patient, via the working channel, along the first axis 140. Similarly, the first robotic arm 110 may be configured to retract the first medical instrument 131 from the patient along the first axis 140 (e.g., the Y-axis) and the second robotic arm 120 may be configured to retract the second medical instrument 133 from the patient, via the working channel, along the first axis 140.

If the first IDM 115 and the second IDM 125 are not properly aligned along the first axis 140, a force may be generated between the first and second IDMs 115 and 125 in the direction of misalignment in the X-Z plane. Accordingly, the first IDM 115 and the second IDM 125 may experience opposite and opposing forces in the X-Z plane due to the misalignment of the first and second IDMs 115 and 125. Further, the forces caused due to misalignment may only be generated while driving one or more of the first and second medical instruments 131 and 133 (e.g., while advancing/inserting the second medical instrument 133 or retracting the first medical instrument 131).

In order to detect a misalignment event, the system may be configured to detect a second force at the second IDM 125 of the second robotic arm 120. The system may determine that at least one of the first force measured at the first IDM 115 and the second force measured at the second IDM 125 is greater than a threshold force. The system may further determine that that the first and second robotic arms 110 and 120 are misaligned in response to determining that both of the first and second forces are greater than the threshold force.

E. Example Collision and Misalignment Detection Technique.

Figure 20:
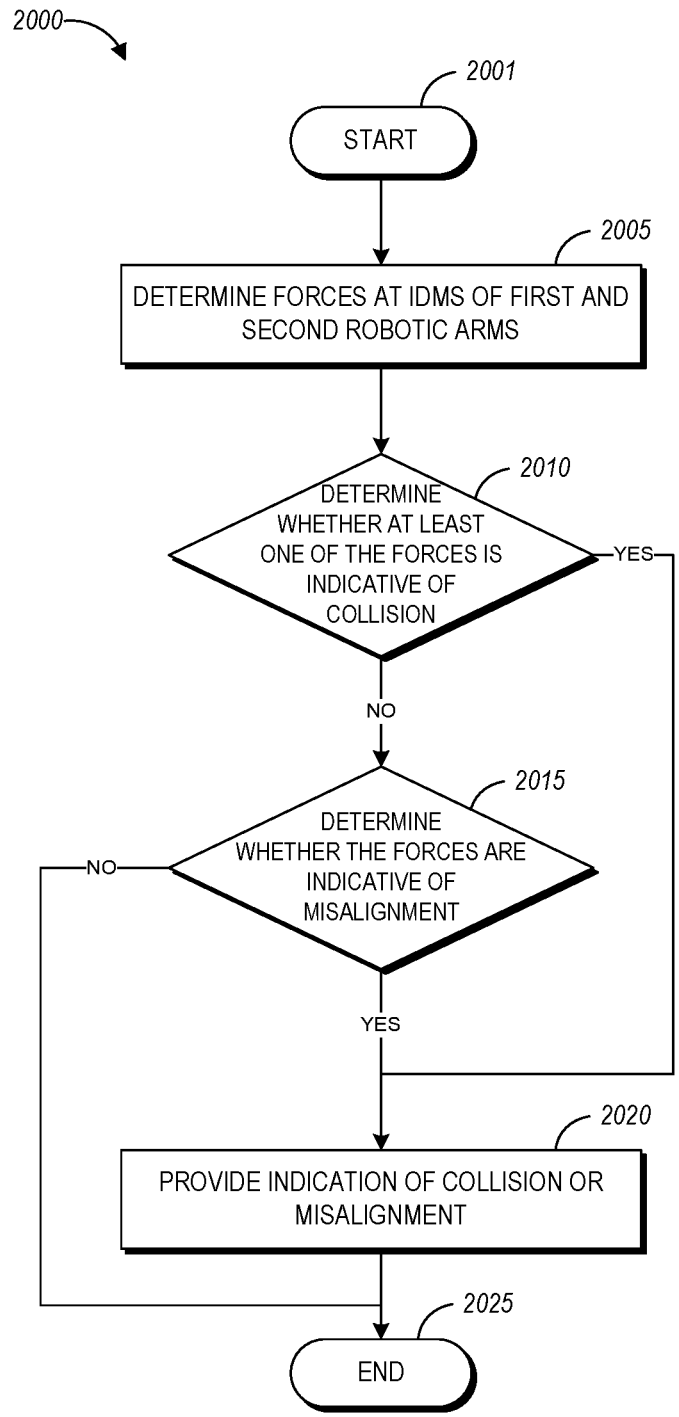
FIG. 20 is a flowchart illustrating an example method operable by a surgical robotic system, or component(s) thereof, for detecting collision or misalignment in accordance with aspects of this disclosure.

In one example implementation, the surgical robotic system may be configured to detect both collision and misalignment events and provide an indication to a user that an event has been detected. FIG. 20 is a flowchart illustrating an example method operable by a surgical robotic system, or component(s) thereof, for detecting collision or misalignment in accordance with aspects of this disclosure. For example, the steps of method 2000 illustrated in FIG. 20 may be performed by a processor and/or other component(s) of a surgical robotic system. For convenience, the method 2000 is described as performed by the processor of the system.

The method 2000 begins at block 2001. At block 2105 the processor determines forces at IDMs of first and second robotic arms. For example, the processor may determine a first force at a first IDM of the first robotic arm and determine a second force at a second IDM of the second robotic arm. The processor may determine the forces based on: i) output received from torque sensors located at each of the joints of the first and second robotic arms and ii) positions of the first and second robotic arms. The first and second forces may be adjusted to remove the forces experienced by the first and second robotic arms due to gravity.

At block 2010, the processor determines whether at least one of the first and second forces is indicative of a collision. For example, the processor may determine whether the first robotic arm has collided with an object based on the first force at the first IDM. Similarly, the processor may determine whether the second robotic arm has collided with an object based on the second force at the second IDM.

In one implementation, the first and/or second robotic arms may be configured to advance a steerable instrument into a patient by movement of the first and/or second IDMs along a first axis. The processor may determine a first component of the first force applied to the first IDM along a second axis perpendicular to the first axis. The processor may determine that the first component of the first force is greater than a first threshold value. Thus, the processor may determine that the first robotic arm has collided with an object based on determining that the first component of the first force is greater than the first threshold value. Since forces along an axis perpendicular to the axis of insertion (e.g., the first axis) are expected to be less than the threshold value, the processor may interpret components of the first force along the perpendicular axis that are greater than the first threshold value to be indicative of a collision. The processor may perform a similar procedure to determine whether the second robotic arm has collided with an object.

The processor may also compare the component of the force along the first axis of insertion to a second threshold. For example, the processor may determine a second component of the first force applied to the IDM along the first axis and determine that the second component of the first force is greater than a second threshold value. The processor may determine that the first robotic arm has collided with the object based on determining that the second component of the first force is greater than the second threshold value, where the second threshold value greater than an expected force of insertion of the steerable instrument into the patient.

In this embodiment, the second threshold may be selected to be greater than the expected force of insertion along the first axis, such that any component of the force measured in the first axis that is greater than the second threshold may be determined to be due to a collision with an object.

In response to determining that the first and second forces are not indicative of a collision, the method 2000 may continue at block 2015, where the processor determines whether the first and second forces are indicative of misalignment. In certain implementations, the processor may determine that both of the first and second forces are greater than a third threshold force and determine that that the first and second robotic arms are misaligned in response to determining that both of the first and second forces are greater than the third threshold force.

The processor may also determine insertion data that indicates that the second medical instrument was being driven (e.g., inserted or retracted) through the first medical instrument at the time that the second force was detected. The insertion data may be stored in the memory and may be determined based on at least one of: the position of the first and second robotic arms and instructions to drive the second medical instrument received from a user. The processor may determine that the first and second robotic arms are misaligned in response to determining that the insertion data indicates that the second medical instrument was being driven (e.g., inserted or retracted) through the first medical instrument. Further, in certain implementations, the processor may determine the forces experienced by the IDMs of the first and second robotic arms are not due to misalignment when the second medical instrument is not being driven through the first medical instrument during measurement of the first and second forces.

In another implementation, the insertion data may indicate that the first medical instrument was being driven at the time that the first and second torque values were measured. The processor may determine that the first force is greater than the threshold value and determine that the first robotic arm is misaligned with a patient introducer in response to determining that the insertion data indicates that the first medical instrument was being driven and determining that the first force is greater than the first threshold value. The patient introducer may be a device configured to guide the first medical instrument into the patient. In certain implementations, the system may be configured to determine a force exerted on the patient introducer. In these implementations, the processor may determine whether the force applied to the patient introducer and the first force are in opposing directions and determine that the first IDM is misaligned with the patient introducer in response to the force applied to the patient introducer and the first force being in opposing directions.

In some embodiments, the processor may be further configured to determine that the first and second forces are in opposing directions. The processor may also determine that a difference between the magnitudes of the first and second forces is less than a threshold difference. The processor may determine that the first and second robotic arms are misaligned in response to determining that the first and second forces are in opposing directions and determining that the difference between the magnitudes of the first and second forces is less than the threshold difference. That the first and second forces having similar magnitudes in opposing directions may be indicative of misalignment since the second medical instrument is coupled to each of the first and second IDMs through the insertion of the second medical instrument into the working channel of the first medical instrument.

In response to determining that one of the first and second robotic arms have collided within an object (in block 2010) or determining that the first and second robotic arm are misaligned, at block 2020, the processor provides an indication of the collision or misalignment. For example, the processor may encode an indication of the collision or misalignment and provide the encoded indication to a display configured to render the encoded data. In certain implementations, the indication may not specify whether the event is a collision or a misalignment. For example, the indication may simply inform the user that a collision/misalignment error has been detected.

In other embodiments, the processor may encode information indicative of the type of event into the indication. For example, the indication may specify at least one of: whether a collision has occurred, which arm(s) are involved in the collision, whether a misalignment has occurred, and which arms are involved in the misalignment.

In response to determining that a collision or misalignment has occurred, the processor may prevent the user from further advancing the steerable instrument into the patient. The indication may further provide instructions to the user to retract the steerable instrument from the patient and reset the system. The processor may also be configured to receive an input from the user indicating that the source of the collision or misalignment has been addressed. In response to receiving an input that the collision or misalignment has been resolved, the processor may allow the user to continue the medical procedure. The method 2000 ends at block 2025.

F. Further Example Collision and Misalignment Technique.

Figure 21:
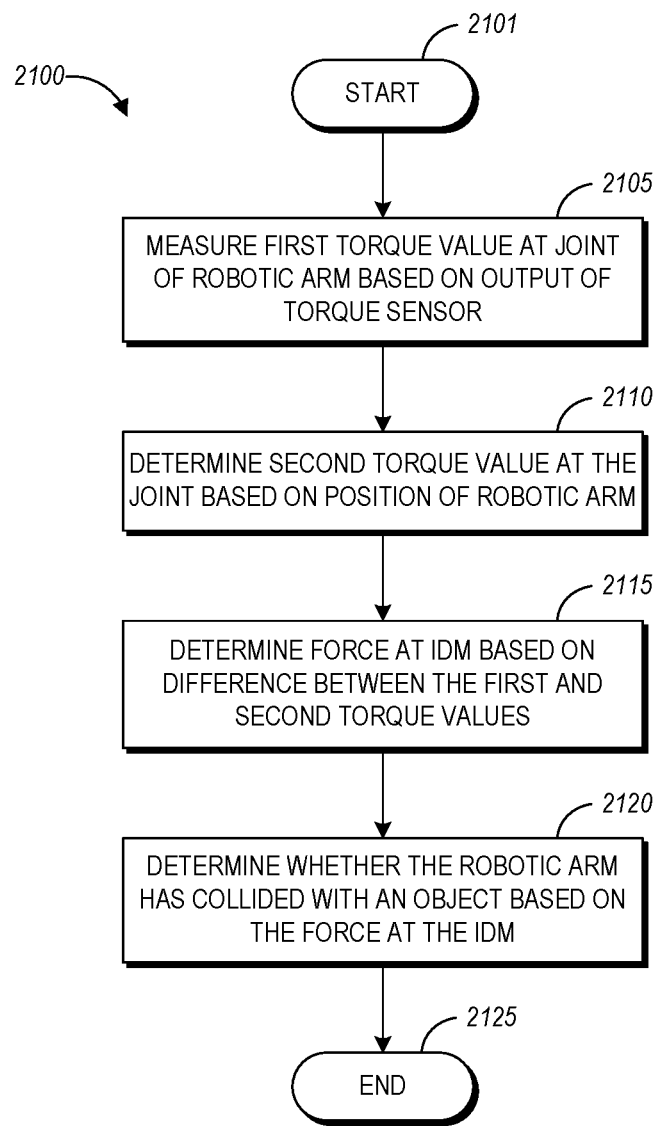
FIG. 21 is a flowchart illustrating an example method operable by a surgical robotic system, or component(s) thereof, for detecting a collision in accordance with aspects of this disclosure.

In one example implementation, the surgical robotic system may be configured to detect a collision of a robotic arm. FIG. 21 is a flowchart illustrating an example method operable by a surgical robotic system, or component(s) thereof, for detecting a collision in accordance with aspects of this disclosure. For example, the steps of method 2100 illustrated in FIG. 21 may be performed by a processor of a surgical robotic system. For convenience, the method 2100 is described as performed by the processor of the system.

The method 2100 begins at block 2101. At block 2105, the processor measures a first torque value at a joint of a robotic arm based on an output of a torque sensor. The robotic arm may include: two linkages connected by the joint, a torque sensor configured to detect torque between the two linkages, and an instrument device manipulator (IDM) connected to a distal end of the robotic arm. At block 2110, the processor determines a second torque value at the joint based on a position of the robotic arm. The second torque value may be indicative of a gravitational component of the torque between the two linkages.

At block 2115, the processor determines a force at the IDM based a difference between the first and second torque values. At block 2120, the processor determines whether the robotic arm has collided with an object based on the force at the IDM. In certain implementations, the processor may provide an indication that the robotic arm has collided with an object in response to determining that the robotic arm has collided with the object. The method ends at block 2125.

3. Implementing Systems and Terminology.

Implementations disclosed herein provide systems, methods and apparatus for detecting a collision or misalignment of one or more robotic arms of a surgical robotic system. This detection may be based on, in certain embodiments, torque measurements performed at the joints of the robotic arm(s).

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The techniques for detection of collision and/or misalignment described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system for detecting misalignment of robotic arms, comprising:
 a first robotic arm comprising a first instrument device manipulator (IDM) connected to a distal end of the first robotic arm;
 a second robotic arm comprising a second IDM connected to a distal end of the second robotic arm;
 a first medical instrument comprising a working channel; and
 a second medical instrument, the first robotic arm configured to drive the first medical instrument along a first axis, and the second robotic arm configured to drive the second medical instrument through the working channel of the first medical instrument;
 a processor; and
 a memory storing computer-executable instructions to cause the processor to:
  determine a first force at the first IDM,
  determine a second force at the second IDM,
  determine that both of the first and second forces are greater than a threshold force, and
  determine that the first and second robotic arms are misaligned in response to the processor determining that both of the first and second forces are greater than the threshold force.

2. The system of claim 1, wherein the memory further stores computer-executable instructions to cause the processor to:
 determine based on insertion data that the second medical instrument was being driven through the first medical instrument at the time that the second force was detected,
 wherein the determination that the first and second robotic arms are misaligned is further in response to the processor determining that the second medical instrument was being driven through the first medical instrument.

3. The system of claim 2, wherein the memory further stores computer-executable instructions to cause the processor to:
 determine based on the insertion data that the first medical instrument was being driven at the time that the first and second IDMs experienced the first and second forces, respectively,
 determine that the first force is greater than the threshold value, and
 determine that the first robotic arm is misaligned with a patient introducer configured to guide the first medical instrument into a patient, in response to the processor determining that the first medical instrument was being driven at the time that the first and second IDMs experienced the first and second forces and determining that the first force is greater than the first threshold value.

4. The system of claim 2, wherein each of the first and second medical instruments comprises one of: a sheath, a leader, a needle, forceps, and a brush.

5. The system of claim 1, wherein the memory further stores computer-executable instructions to cause the processor to:
 determine that the first and second forces are in opposing directions, and
 determine that a difference between the magnitudes of the first and second forces is less than a threshold difference,
 wherein the determination that the first and second robotic arms are misaligned is further in response to the processor determining that the first and second forces are in opposing directions and that the difference between the magnitudes of the first and second forces is less than the threshold difference.

6. The system of claim 1, wherein each of the first and second robotic arms comprises:
 at least two linkages,
 at least one joint connecting the at least two linkages, and
 at least one torque sensor configured to detect torque between the at least two linkages.

7. The system of claim 6, wherein the memory further stores computer-executable instructions to cause the processor to:
 measure a first torque value at the at least one joint of the first robotic arm based on an output of the torque sensor,
 determine a second torque value at the at least one joint of the first robotic arm based on a position of the first robotic arm, the second torque value indicative of a gravitational component of the torque between the at least two linkages,
 determine a first force at the first IDM based on a difference between the first and second torque values, and
 determine, based on the first force at the first IDM, whether a collision has occurred between the first robotic arm and an object.

8. The system of claim 7, wherein the memory further stores computer-executable instructions to cause the processor to:
 encode an indication of the collision between the first robotic arm and the object, and
 provide the encoded indication of the collision to a display configured to render encoded data.

9. The system of claim 7, wherein the memory further stores computer-executable instructions to cause the processor to:
 determine a first component of the first force applied to the first IDM along a second axis perpendicular to the first axis, and
 determine that the first component of the first force is greater than a first threshold value,
 wherein the determining of the collision is further based on the processor determining that the first component of the first force is greater than the first threshold value.

10. The system of claim 9, wherein the memory further stores computer-executable instructions to cause the processor to:
 determine a second component of the first force applied to the IDM along the first axis, and
 determine that the second component of the first force is greater than a second threshold value,
 wherein the determining of the collision is further based on the processor determining that the second component of the first force is greater than the second threshold value, the second threshold value greater than an expected force of insertion of the first medical instrument.

11. A non-transitory computer readable storage medium having stored thereon instructions that, when executed, cause at least one computing device to:

determine a first force at a first IDM connected to a distal end a first robotic arm;

determine a second force at a second IDM connected to a distal end a second robotic arm, the first robotic arm configured to drive a first medical instrument comprising a working channel along a first axis, and the second robotic arm configured to drive a second medical instrument through the working channel of the first medical instrument;

determine that both of the first and second forces are greater than a threshold force; and determine that the first and second robotic arms are misaligned in response to the determination that both of the first and second forces are greater than the threshold force.

12. The non-transitory computer readable storage medium of claim 11, further having stored thereon instructions that, when executed, cause at least one computing device to:

determine based on insertion data that the second medical instrument was being driven through the first medical instrument at the time that the second force was detected, wherein the determination that the first and second robotic arms are misaligned is further in response to the determination that the second medical instrument was being driven through the first medical instrument.

13. The non-transitory computer readable storage medium of claim 12, further having stored thereon instructions that, when executed, cause at least one computing device to:

determine based on the insertion data that the first medical instrument was being driven at the time that the first and second IDMs experienced the first and second forces, respectively;

determine that the first force is greater than the threshold value; and determine that the first robotic arm is misaligned with a patient introducer configured to guide the first medical instrument into a patient in response to the determination that the first medical instrument was being driven at the time that the first and second IDMs experienced the first and second forces and determining that the first force is greater than the first threshold value.

14. The non-transitory computer readable storage medium of claim 12, wherein each of the first and second medical instruments comprise one of: a sheath, a leader, a needle, forceps, and a brush.

15. The non-transitory computer readable storage medium of claim 11, further having stored thereon instructions that, when executed, cause at least one computing device to:

determine that the first and second forces are in opposing directions; and determine that a difference between the magnitudes of the first and second forces is less than a threshold difference, wherein the determination that the first and second robotic arms are misaligned is further in response to the determination that the first and second forces are in opposing directions and that the difference between the magnitudes of the first and second forces is less than the threshold difference.

16. The non-transitory computer readable storage medium of claim 11, wherein each of the first and second robotic arms comprises:

at least two linkages, at least one joint connecting the at least two linkages, and at least one torque sensor configured to detect torque between the at least two linkages.

17. The non-transitory computer readable storage medium of claim 16, further having stored thereon instructions that, when executed, cause at least one computing device to:

measure a first torque value at the at least one joint of the first robotic arm based on an output of the torque sensor;

determine a second torque value at the at least one joint of the first robotic arm based on a position of the first robotic arm, the second torque value indicative of a gravitational component of the torque between the at least two linkages;

determine a first force at the first IDM based on a difference between the first and second torque values; and determine, based on the first force at the first IDM, whether a collision has occurred between the first robotic arm and an object.

18. The non-transitory computer readable storage medium of claim 17, further having stored thereon instructions that, when executed, cause at least one computing device to:

encode an indication of the collision between the first robotic arm and the object; and provide the encoded indication of the collision to a display configured to render encoded data.

19. The non-transitory computer readable storage medium of claim 17, further having stored thereon instructions that, when executed, cause at least one computing device to:

determine a first component of the first force applied to the first IDM along a second axis perpendicular to the first axis; and determine that the first component of the first force is greater than a first threshold value, wherein the determining of the collision is further based on determining that the first component of the first force is greater than the first threshold value.

20. The non-transitory computer readable storage medium of claim 19, further having stored thereon instructions that, when executed, cause at least one computing device to:

determine a second component of the first force applied to the IDM along the first axis; and determine that the second component of the first force is greater than a second threshold value, wherein the determining of the collision is further based on determining that the second component of the first force is greater than the second threshold value, the second threshold value greater than an expected force of insertion of the first medical instrument.

21. A method of positioning a first robotic arm, comprising:

determining a first force at a first IDM connected to a distal end of a first robotic arm;

determining a second force at a second IDM connected to a distal end of a second robotic arm, the first robotic arm configured to drive a first medical instrument comprising a working channel along a first axis, and the second robotic arm configured to drive a second medical instrument through the working channel of the first medical instrument;

determining that both of the first and second forces are greater than a threshold force; and determining that the first and second robotic arms are misaligned in response to the determination that both of the first and second forces are greater than the threshold force.

22. The method of claim 21, further comprising:
determining, based on insertion data, that the second medical instrument was being driven through the first medical instrument at the time that the second force was detected,
wherein the determination that the first and second robotic arms are misaligned is further in response to the determination that the second medical instrument was being driven through the first medical instrument.

23. The method of claim 22, further comprising:
determining, based on the insertion data, that the first medical instrument was being driven at the time that the first and second IDMs experienced the first and second forces, respectively;
determining that the first force is greater than the threshold value; and
determining that the first robotic arm is misaligned with a patient introducer configured to guide the first medical instrument into a patient, in response to the determination that the first medical instrument was being driven at the time that the first and second IDMs experienced the first and second forces and that the first force is greater than the first threshold value.

24. The method of claim 22, wherein each of the first and second medical instruments comprise one of: a sheath, a leader, a needle, forceps, and a brush.

25. The method of claim 21, further comprising:
determining that the first and second forces are in opposing directions; and
determining that a difference between the magnitudes of the first and second forces is less than a threshold difference,
wherein the determination that the first and second robotic arms are misaligned is further in response to the determination that the first and second forces are in opposing directions and that the difference between the magnitudes of the first and second forces is less than the threshold difference.

26. The method of claim 21, wherein each of the first and second robotic arms comprises:
at least two linkages,
at least one joint connecting the at least two linkages, and
at least one torque sensor configured to detect torque between the at least two linkages.

27. The method of claim 26, further comprising:
measuring a first torque value at the at least one joint of the first robotic arm based on an output of the torque sensor;
determining a second torque value at the at least one joint of the first robotic arm based on a position of the first robotic arm, the second torque value indicative of a gravitational component of the torque between the at least two linkages;
determining a first force at the first IDM based on a difference between the first and second torque values; and
determining, based on the first force at the first IDM, whether a collision has occurred between the first robotic arm and an object.

28. The method of claim 27, further comprising:
encoding an indication of the collision between the first robotic arm and the object; and
providing the encoded indication of the collision to a display configured to render encoded data.

29. The method of claim 26, further comprising:
determining a first component of the first force applied to the first IDM along a second axis perpendicular to the first axis; and
determining that the first component of the first force is greater than a first threshold value,
wherein the determining of the collision is further based on determining that the first component of the first force is greater than the first threshold value.

30. The method of claim 29, further comprising:
determining a second component of the first force applied to the IDM along the first axis; and
determining that the second component of the first force is greater than a second threshold value,
wherein the determining of the collision is further based on determining that the second component of the first force is greater than the second threshold value, the second threshold value greater than an expected force of insertion of the first medical instrument.

* * * * *